(12) United States Patent
Inoue et al.

(10) Patent No.: US 11,261,244 B2
(45) Date of Patent: Mar. 1, 2022

(54) ANTIBODY AGAINST HUMAN TGF-β LAP DEGRADATE, AND USE THEREOF

(71) Applicants: RIKEN, Wako (JP); THE JIKEI UNIVERSITY, Tokyo (JP); SYSMEX CORPORATION, Kobe (JP)

(72) Inventors: Ikuyo Inoue, Wako (JP); Soichi Kojima, Wako (JP); Mikako Shirouzu, Wako (JP); Chiemi Tsumagari, Wako (JP); Takehisa Matsumoto, Wako (JP); Takashi Saito, Wako (JP); Toshitada Takemori, Wako (JP); Tomokazu Matsuura, Tokyo (JP); Takahiro Masaki, Tokyo (JP); Masahiro Miura, Kobe (JP); Kozo Suto, Kobe (JP)

(73) Assignees: RIKEN, Wako (JP); THE JIKEI UNIVERSITY, Tokyo (JP); SYSMEX CORPORATION, Kobe (JP)

( * ) Notice: Subject to any disclaimer, the term of this patent is extended or adjusted under 35 U.S.C. 154(b) by 11 days.

(21) Appl. No.: 16/931,788

(22) Filed: Jul. 17, 2020

(65) Prior Publication Data
US 2021/0017265 A1    Jan. 21, 2021

(30) Foreign Application Priority Data

Jul. 19, 2019    (JP) .............................. JP2019-133839

(51) Int. Cl.
*C07K 16/22* (2006.01)
*G01N 33/53* (2006.01)

(52) U.S. Cl.
CPC .............. *C07K 16/22* (2013.01); *G01N 33/53* (2013.01); *C07K 2317/565* (2013.01)

(58) Field of Classification Search
None
See application file for complete search history.

(56) References Cited

U.S. PATENT DOCUMENTS

2011/0071278 A1    3/2011    Kojima et al.

FOREIGN PATENT DOCUMENTS

| WO | 2011102483 A1 | 8/2011 | |
|---|---|---|---|
| WO | WO-2016115345 A1 * | 7/2016 | .............. A61P 35/00 |
| WO | 2020/076969 A2 | 4/2020 | |

OTHER PUBLICATIONS

Vajdos et al. (J Mol Biol. Jul. 5, 2002;320(2):415-28) (Year: 2002).*
Brown et al. (J Immunol. May 1996;156(9):3285-91) (Year: 1996).*
Zhao et al (Antibodies (Basel). Jun. 29, 2018;7(3):22) (Year: 2018).*
M. Hara et al., "LAP degradation product reflects plasma kallikrein-dependent TGF-ß activation in patients with hepatic fibrosis", SpringerPlus, 2014, vol. 3, No. 221, Published on May 1, 2014, pp. 1-11 (11 Pages total).
BioLegend, Inc., "APC anti-mouse LAP (TGF-ß1) Antibody", Revision Date: Aug. 27, 2014, Downloaded from <https://www.biolegend.com/fr-ch/products/apc-anti-mouse-lap-tgf-beta1-antibody-7310>(4 Pages total).
ThermoFisher, "LAP Antibodies", retrieved on May 28, 2019, from <https://www.thermofisher.com/antibody/primary/target/lap> (3 pages total).
Cosmo Bio Co., Ltd., "anti TGF-ß1 LAP-D (L59) (LAP Degradates N-Terminus side cut end L59)", retrieved on Oct. 13, 2020, Catalog No. RIK-MA-L59, Version#180326 (2 pages total).
Extended European Search Report, dated Nov. 24, 2020, issued by the European Patent Office in European Patent Application No. 20186354.5.
BioLegend, "APC anti-human LAP (TGF-ß1) Antibody Clone TW4-2F8", Version 2, Mar. 23, 2016, XP055749591 (3 pages total).
R&D Systems, Inc., "Quantikine ELISA Human LAP (TGF-ß1) Immunoassay", Jan. 1, 2019, XP055749643 (16 pages total).
Dong et al., "Force Interacts with Macromolecular Structure in Activation of TGF-ß", Nature, 2017, vol. 542, No. 7639, pp. 55-59 (30 pages total).

* cited by examiner

*Primary Examiner* — Brian Gangle
*Assistant Examiner* — Andrea K McCollum
(74) *Attorney, Agent, or Firm* — Sughrue Mion, PLLC

(57) ABSTRACT

Disclosed is an isolated monoclonal antibody against a human Transforming Growth Factor-β (TGF-β) Latency Associated Protein (LAP) degradate, the isolated monoclonal antibody being capable of recognizing an integrin binding site in the human TGF-β LAP degradate.

12 Claims, 9 Drawing Sheets

Specification includes a Sequence Listing.

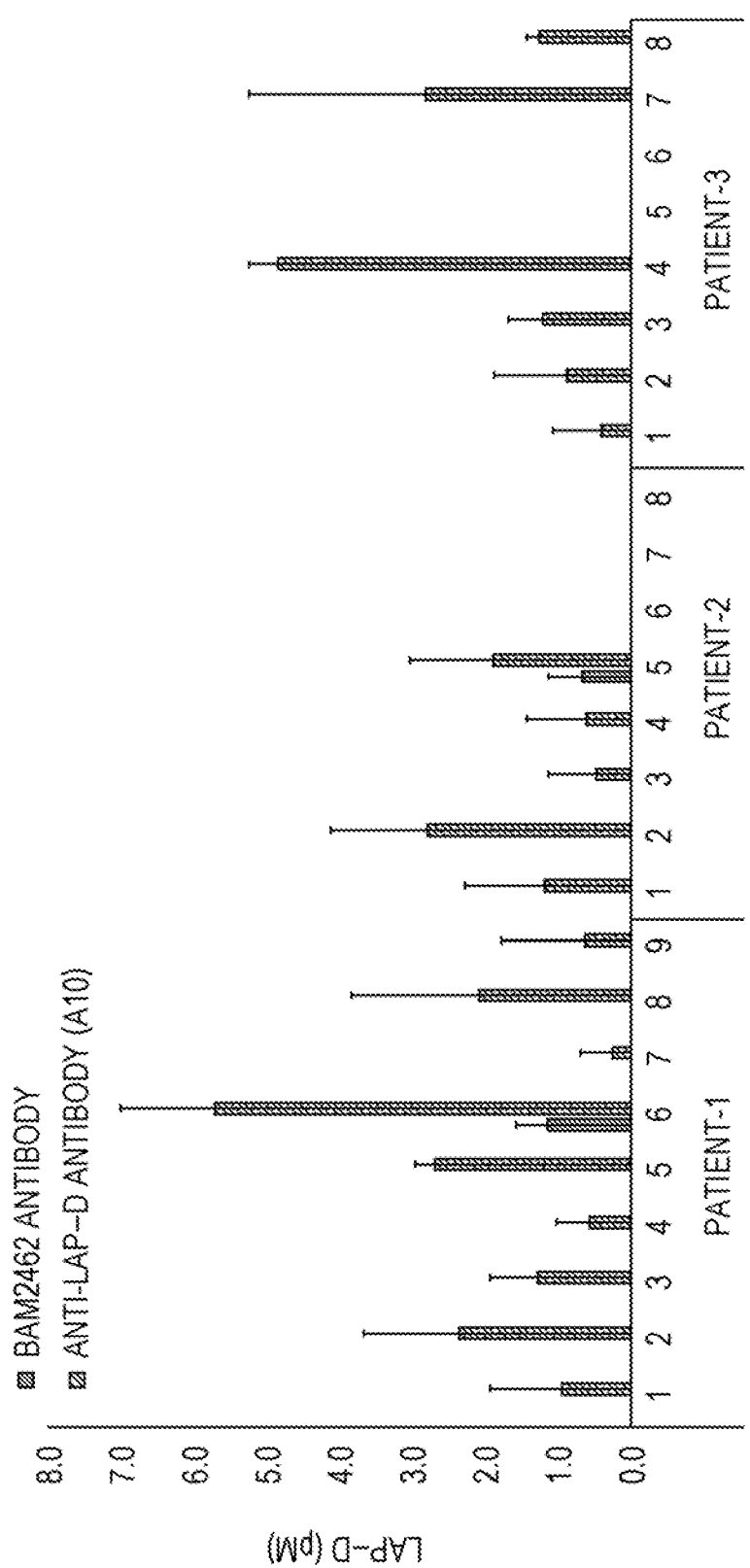

ANTIBODY AGAINST HUMAN TGF-β LAP DEGRADATE, AND USE THEREOF

CROSS REFERENCE TO RELATED APPLICATIONS

This application claims priority from prior Japanese Patent Application No. 2019-133839, filed on Jul. 19, 2019, entitled "ANTIBODY AGAINST HUMAN TGF-β LAP DEGRADATE, AND USE THEREOF", the entire contents of which are incorporated herein by reference.

FIELD OF THE INVENTION

The present invention relates to an isolated monoclonal antibody capable of recognizing an integrin binding site in a human transforming growth factor (TGF)-β LAP degradate. The present invention also relates to a reagent for use in detection of a LAP degradate, which comprises the antibody. The present invention further relates to a method for measuring a LAP degradate in a biological sample and a method for monitoring a measurement value for the LAP degradate, in each of which the antibody is used.

BACKGROUND

TGF-β is a cytokine exhibiting various biological activities, and is involved in clinical conditions such as liver fibrosis. TGF-β is produced in the form of a latent complex in which TGF-β is trapped in a prepeptide moiety called "latency associate protein (LAP)". Activated TGF-β is released from the latent complex through some kind of activation reaction. For example, as illustrated in FIG. 1, in an activation reaction with plasma kallikrein (PLK) that is a serine protease, LAP in the latent complex is cut at a site between an arginine residue at position-58 and a leucine residue at position-59 to release activated TGF-β. In this activation reaction, a LAP degradate (LAP-D) is produced as a byproduct. U.S. Patent Application Publication No. 2011/0071278 discloses that an anti-LAP-D antibody specifically recognizing a cut face of LAP with PLK is produced and a human LAP-D is measured by a sandwich ELISA method using the antibody and a commercially available anti-LAP antibody.

In U.S. Patent Application Publication No. 2011/0071278, although a recombinant LAPβ1 (human TGF-β1 LAP) protein treated with PLK is measured as a LAP-D, the measurement of a LAP-D in a clinical specimen, e.g., plasma, collected from a subject is not carried out. The LAP-D may be further degraded in vivo, or the LAP-D may not occur in a quantity sufficient for the detection in the clinical specimen. Actually, the present inventors measured a LAP-D in a plasma specimen collected from a patient having hepatitis C virus infection using the antibody disclosed in U.S. Patent Application Publication No. 2011/0071278 and a commercially available anti-LAP antibody, and it was found that there was a specimen that could not be measured and a specimen having a very small measurement value. In these situations, the present invention addresses the problem of providing an anti-LAP-D antibody which enables the measurement of a LAP-D with improved detectability.

SUMMARY OF THE INVENTION

The scope of the present invention is defined solely by the appended claims, and is not affected to any degree by the statements within this summary.

The present invention provides: an isolated monoclonal antibody against a human TGF-β LAP degradate, wherein the isolated monoclonal antibody recognizes an integrin binding site in the human TGF-β LAP degradate; and a use of the isolated monoclonal antibody. The present invention also provides a reagent for use in detection of a LAP degradate, comprising the isolated monoclonal antibody. The present invention further provides a reagent kit for use in detection of a LAP degradate, comprising: a first reagent which comprises the isolated monoclonal antibody; and a second reagent which comprises an antibody specifically recognizing a region comprising a leucine residue located at the N-terminal of the amino acid sequence of SEQ ID NO: 3.

The present invention still further provides a method for measuring a human TGF-β LAP degradate, comprising measuring a TGF-β LAP degradate in a biological sample collected from a subject using the isolated monoclonal antibody.

The present invention still further provides a method for monitoring a measurement value for a human TGF-β LAP degradate, comprising: measuring a TGF-β LAP degradate in a first biological sample collected from a subject using the isolated monoclonal antibody; and measuring the TGF-β LAP degradate in a second biological sample collected from the subject using the isolated monoclonal antibody, wherein the first biological sample is a biological sample collected from the subject at a first point of time and the second biological sample is a biological sample collected from the subject at a second point of time that is different from the first point of time.

According to the present invention, there are provided: an isolated monoclonal antibody against a human TGF-β LAP degradate, which enables the measurement of a human TGF-β LAP degradate with improved detectability; and a use of the isolated monoclonal antibody.

BRIEF DESCRIPTION OF THE DRAWINGS

FIG. 6A is a graph showing the concentration of a LAP-D in a plasma specimen, which is produced by the measurement using the isolated monoclonal antibody of the present embodiment and an anti-human LAP TGF-β1 antibody (BAM2462, manufactured by R&D Systems) as detection antibodies;

DETAILED DESCRIPTION OF THE PREFERRED EMBODIMENTS

[1. Isolated Monoclonal Antibody Against Human TGF-β LAP Degradate]

The isolated monoclonal antibody (also simply referred to as "antibody", hereinafter) against a human TGF-β LAP degradate according to the present embodiment recognizes an integrin binding site in the human TGF-β LAP degradate and can bind specifically to the human TGF-β LAP degradate.

The term "LAP" as used herein refers to a dimeric prepeptide moiety that is associated with activated TGF-β in a latent complex of human TGF-β through hydrophobic bonding. The term "human TGF-β LAP degradate" (or "LAP degradate of human TGF-β") as used herein refers to a degradation product of LAP which is produced by cutting out LAP in the latent complex of human TGF-β (wherein the LAP is also referred to as "human TGF-β LAP" or "LAP of human TGF-β", hereinafter) with a protease. The human TGF-β LAP degradate (or LAP degradate of human TGF-β) is also simply referred to as "LAP-D" or "LAP degradate", hereinafter. The term "isolated monoclonal antibody" as used herein refers to a monoclonal antibody which is isolated and/or collected from a component occurring in a natural environment and does not substantially contain another antibody having different antigen specificity.

Human TGF-β includes three isoforms, i.e., TGF-β1, TGF-β2 and TGF-β3. The antibody of the present embodiment may bind to a LAP-D of any human TGF-β isoform, and preferably binds to a LAP-D of human TGF-β1. Each of the TGF-β isoforms is originally synthesized in the form of a precursor polypeptide composed of a moiety that serves as activated TGF-β and LAP that is a prepeptide moiety. The amino acid sequence for the precursor polypeptide of human TGF-β1 is shown in SEQ ID NO: 1. The precursor polypeptide of human TGF-β1 is composed of 390 amino acid residues. In the amino acid sequence of SEQ ID NO: 1, a moiety lying between an amino acid residue at position-30 and an amino acid residue at position-278 is human TGF-β1 LAP (monomer) and a moiety lying between an amino acid residue at position-279 and an amino acid residue at position-390 is a moiety that serves as activated TGF-β1 (a monomer of activated TGF-β1). The amino acid sequence for human TGF-β1 LAP (monomer) is shown in SEQ ID NO: 2.

Figure 1:
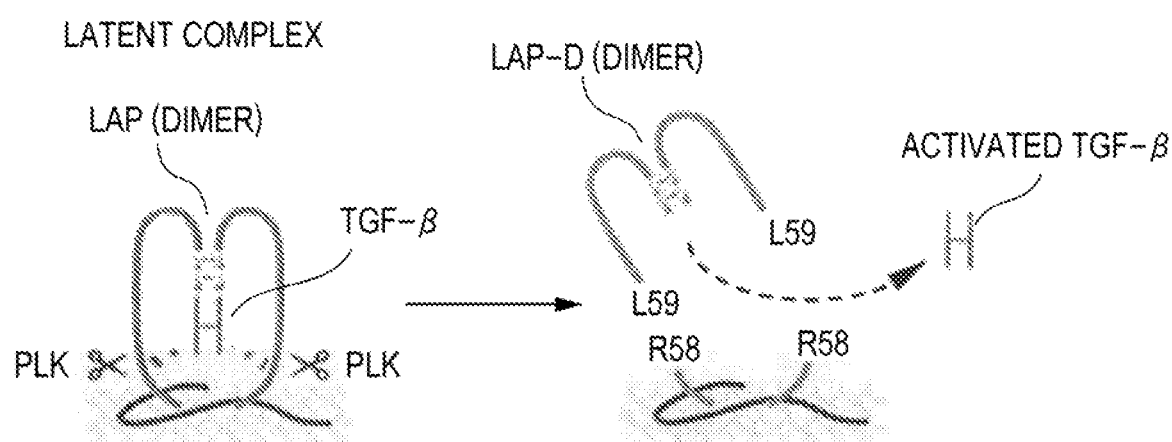
FIG. 1 is a schematic diagram showing the activation reaction of a latent complex of TGF-β with PLK.

The precursor polypeptide of TGF-β is cut in a golgi body and is separated into a moiety that serves as activated TGF-β and LAP. The separated LAP moieties together form a dimer through a disulfide bond. The separated moieties each serving as activated TGF-β also together form a dimer, thereby forming activated TGF-β. However, activated TGF-β is trapped by the dimeric LAP and is secreted in the form of a latent complex as shown in FIG. 1. By cutting the LAP dimer with a protease, activated TGF-β is released and, as a result, LAP-D is produced. It is considered that the LAP-D immediately after the production thereof occurs in the form of a dimer. However, the LAP-D may be converted to a monomer in vivo thereafter. The antibody of the present embodiment may bind to either one of a dimeric LAP-D or a monomeric LAP-D.

The LAP-D to which the antibody of the present embodiment can bind may be produced from LAP using any protease, as long as the LAP-D has an integrin binding site. It is preferred that the LAP-D is produced using a protease capable of cutting human TGF-β LAP to release activated TGF-β. As the protease, for example, plasma kallikrein (PLK), plasmin, matrix metalloproteinase (MMP) 3 and MMP9 are known. Among these proteases, PLK is particularly preferred. It is known that PLK can cut LAP at a site located between an arginine residue at position-58 and a leucine residue at position-59 in the amino acid sequence of SEQ ID NO: 1. In the case where human TGF-β1 LAP is cut with PLK, the amino acid sequence for a monomeric LAP-D is a sequence of SEQ ID NO: 3.

The term "integrin binding site" as used herein refers to a region which lies on human TGF-β LAP and includes a site capable of being recognized by integrin. It is known that the structure of LAP is changed upon the binding of LAP in the latent complex to integrin to release activated TGF-β. A LAP-D produced by the TGF-β activation reaction also has an integrin binding site. In the present embodiment, it does not matter whether or not the LAP-D can bind to integrin through the integrin binding site. In the present embodiment, it is preferred that the integrin binding site in the LAP-D includes an RGD sequence (i.e., a sequence composed of an arginine residue, a glycine residue and an aspartic acid residue). It is particularly preferred that the integrin binding site in the LAP-D is a region which is included in LAP-D and composed of 4 to 10 amino acid residues including an RGD sequence or a region consisting of an RGD sequence.

It is preferred that the antibody of the present embodiment recognizes, as an integrin binding site of LAP-D, a region which is included in a human TGF-β1 LAP-D and includes the amino acid residues at position-215 to position-217 (i.e., an RGD sequence) in the amino acid sequence of SEQ ID NO: 2. It is particularly preferred that the antibody of the present embodiment recognizes a region which is included in a human TGF-β1 LAP-D and is composed of 4 to 10 amino acid residues including the amino acid residues at position-215 to position-217 (i.e., an RGD sequence) in the amino acid sequence of SEQ ID NO: 2, or a region which is composed of the amino acid residues lying between the amino acid residue at position-215 and the amino acid residue at position-217 in the amino acid sequence of SEQ ID NO: 2.

The antibody of the present embodiment may be a monoclonal antibody originated from any mammal such as mouse, rat, hamster, rabbit, goat and horse, and is preferably a monoclonal antibody originated from mouse. The class of the antibody of the present embodiment may be any one selected from IgG, IgA, IgM, IgD and IgE, and is preferably IgG. The subclass of the IgG is not particularly limited, and may be any one selected from IgG1, IgG2, IgG3 and IgG4. The antibody of the present embodiment may be in the form of an immunoglobulin as well as an antibody fragment. Examples of the antibody fragment include Fab, F(ab')2, Fab', Fv, Fd, a domain antibody (dAb), a single-chain antibody (scFv) and a diabody. Among these antibody fragments, Fab is preferred.

It is preferred that the antibody of the present embodiment may compete with a specific reference antibody for the binding to human TGF-β LAP-D, preferably the binding to human TGF-β1 LAP-D. In the reference antibody, there are three complementarity determining regions (CDRs) in each of a heavy chain variable region and a light chain variable region. The three CDRs are named CDR1, CDR2 and CDR3 arranged from the amino terminal of the antibody chain. In the present embodiment, the reference antibody comprises: a light chain comprising CDR1, CDR2 and CDR3 respectively consisting of the below-mentioned amino acid sequences (SEQ ID NOs: 4, 5 and 6); and a heavy chain comprising CDR1, CDR2 and CDR3 respectively consisting of the below-mentioned amino acid sequences (SEQ ID NOs: 7, 8 and 9). The amino acid sequences for these CDRs are sequences in accordance with the Kabat classification (Wu T T. and Kabat E A., 1970, J. Exp. Med. 132:211-250). The reference antibody is an isolated monoclonal antibody capable of binding to an integrin binding site in a human TGF-β1 LAP-D, but is not included within the scope of the antibody of the present embodiment.

[Amino Acid Sequences for CDRs of Reference Antibody]

```
Light chain CDR1:
                              (SEQ ID NO: 4)
SASSSVSYMH

Light chain CDR2:
                              (SEQ ID NO: 5)
STSNLAS

Light chain CDR3:
                              (SEQ ID NO: 6)
QQRSSYPFT

Heavy chain CDR1:
                              (SEQ ID NO: 7)
SYWMN

Heavy chain CDR2:
                              (SEQ ID NO: 8)
MIDPSDSETHYNQMFKD Heavy chain CDR3:
                              (SEQ ID NO: 9)
WPYALDY
```

It is preferred that the reference antibody comprises: a light chain comprising a variable region consisting of the amino acid sequence (SEQ ID NO: 10) shown below; and a heavy chain comprising a variable region consisting of the amino acid sequence (SEQ ID NO: 11) shown below. The reference antibody having these variable regions is a mouse-originated monoclonal antibody.

[Amino Acid Sequences for Variable Regions of Reference Antibody]

```
Light chain variable region
                              (SEQ ID NO: 10)
QIVLTQSPAIMSASPGEKVTMTCSASSSVSYMHWFQQKPGTSPKLWIYS
TSNLASGVPARFSGSGSGTSYSLTISRMEAEDAATYYCQQRSSYPFTFGS
GTKLEIKRA
```

```
Heavy chain variable region
                              (SEQ ID NO: 11)
EVQLQQSGAELVRPGASVKLSCKASGYTFTSYWMNWVKQRPGQGLE
WIGMIDPSDSETHYNQMFKDKATLTVDKSSSTAYMQLSSLTSEDSAVYYC
VNWPYALDYWGQGTSVTVSS
```

The wording "the antibody of the present embodiment 'competes with the reference antibody' for the binding to a LAP-D" refers to the matter that a binding site for the antibody of the present embodiment on the LAP-D and a binding site for the reference antibody on the LAP-D are identical to each other or the matter that the antibody of the present embodiment can bind to a site on the LAP-D which is a steric hindrance to the binding between the reference antibody and the LAP-D. In other words, the antibody of the present embodiment recognizes an epitope that is completely or partially identical to an epitope of the reference antibody.

The competition between the antibody of the present embodiment and the reference antibody for the binding to a LAP-D can be evaluated by a surface plasmon resonance (SPR) analysis. The SPR analysis can be carried out using, for example, an SPR analysis device. An example of the analysis device is BIACORE (registered trademark) device. In the analysis, the reference antibody may be in the form of an antibody fragment such as Fab. For example, with respect to the binding of the antibody of the present embodiment to a LAP-D, the maximal binding response value (also referred to as "Rmax value", hereinafter) measured using BIACORE (registered trademark) device is decreased by at least 70%, preferably at least 75%, due to the presence of a reference antibody. In other words, the Rmax value of binding between the antibody of the present embodiment and a LAP-D in the presence of a reference antibody is decreased by at least 70%, preferably at least 75%, compared with the Rmax value of binding between the antibody of the present embodiment and the LAP-D in the absence of the reference antibody. The Rmax value is a maximum value of the response measured using BIACORE (registered trademark) device, and is a value that is not adjusted with taking the molecular weight of an antigen (analyte) immobilized on a sensor chip into consideration. The conditions for the measurement using BIACORE (registered trademark) device are those mentioned in Example 4. In the measurement using BIACORE (registered trademark) device, the value of response is expressed in RU (Resonance Unit).

In the antibody of the present embodiment, there are three CDRs in each of the heavy chain and light chain variable regions. It is preferred that the antibody of the present embodiment comprises a light chain comprising CDR1, CDR2 and CDR3 respectively consisting of the amino acid sequences (SEQ ID NOs: 12, 13 and 14) shown below. It is preferred that the antibody of the present embodiment comprises a heavy chain comprising CDR1, CDR2 and CDR3 respectively consisting of the amino acid sequences (SEQ ID NOs: 15, 16 and 17) shown below. The amino acid sequences for these CDRs are sequences according to the Kabat classification. The antibody of the present embodiment which has these CDRs can bind specifically to a human TGF-β1 LAP-D.

[Amino Acid Sequences for CDRs of Antibody of the Present Embodiment]

Light chain CDR1:
(SEQ ID NO: 12)
RASHEISGYLG

Light chain CDR2:
(SEQ ID NO: 13)
AASTLDS

Light chain CDR3:
(SEQ ID NO: 14)
LQYASYPFT

Heavy chain CDR1:
(SEQ ID NO: 15)
RFWMN

Heavy chain CDR2:
(SEQ ID NO: 16)
MIHSSDSITRLNQKFKD

Heavy chain CDR3:
(SEQ ID NO: 17)
GYDEYSAMDY

In the case where the antibody of the present embodiment is a monoclonal antibody originated from mouse, it is preferred that the antibody comprises a light chain comprising a variable region consisting of the amino acid sequence (SEQ ID NO: 18) shown below. It is also referred that the antibody comprises a heavy chain comprising a variable region consisting of the amino acid sequence (SEQ ID NO: 19) shown below. The antibody of the present embodiment which has these variable regions can bind specifically to a human TGF-β1 LAP-D.

[Amino Acid Sequences for Variable Regions of Antibody of the Present Embodiment]

Light chain variable region
(SEQ ID NO: 18)
DIQMTQSPSSLSASLGERVSLTCRASHEISGYLGWLQRQPDGTIKRLIYA
ASTLDSGVPKRFSGSRSGSDYSLTISSLESEDFADYYCLQYASYPFTFGS
GTKLEVKRA Heavy chain variable region
(SEQ ID NO: 19)
QVQLQQPGAELVRPGASVKLSCKTSGYSFTRFWMNWVRQRPGQGLE
WIGMIHSSDSITRLNQKFKDKATLTLDYSSSTAYMQLSSPTSEDSAVYYC
ARGYDEYSAMDYWGQGTSVPVSS In the case where the antibody of the present embodiment is a monoclonal antibody originated from mouse, it is preferred that the antibody comprises a light chain comprising the amino acid sequence (SEQ ID NO: 20) shown below. It is also referred that the antibody comprises a heavy chain comprising the amino acid sequence (SEQ ID NO: 21) shown below. The antibody of the present embodiment which has these variable regions can bind specifically to a human TGF-β1 LAP-D.

[Amino Acid Sequences for Light Chain and Heavy Chain of Antibody of the Present Embodiment]

Light chain
(SEQ ID NO: 20)
MDMRVPAHVFGLLLLWFPGTRCDIQMTQSPSSLSASLGERVSLTCRAS

HEISGYLGWLQRQPDGTIKRLIYAASTLDSGVPKRFSGSRSGSDYSLTIS

SLESEDFADYYCLQYASYPFTFGSGTKLEVKRADAAPTVSIFPPSSEQLT

SGGASVVCFLNNFYPKDINVKWKIDGSERQNGVLNSWTDQDSKDSTYSMS

STLTLTKDEVERHNSYTCEATHKTSTSPIVKSFNRNEC

Heavy chain
(SEQ ID NO: 21)
MGWSSIILFLVATATGVHSQVQLQQPGAELVRPGASVKLSCKTSGYSF

TRFWMNWVRQRPGQGLEWIGMIHSSDSITRLNQKFKDKATLTLDYSSSTA

YMQLSSPTSEDSAVYYCARGYDEYSAMDYWGQGTSVPVSSAKTTPPSVYP

LAPGSAAQTNSMVTLGCLVKGYFPEPVTVTWNSGSLSSGVHTFPAVLQSD

LYTLSSSVTVPSSTWPSETVTCNVAHPASSTKVDKKIVPRDCGCKPCICT

VPEVSSVFIFPPPKPKDVLTITLTPKVTCVVVDISKDDPEVQFSWFVDDVE

VHTAQTQPREEQFNSTFRSVSELPIMHQDWLNGKEFKCRVNSAAFPAPIE

KTISKTKGRPKAPQVYTIPPPKEQMAKDKVSLTCMITDFFPEDITVEWQW

NGQPAENYKNTQPIMDTDGSYFVYSKLNVQKSNWEAGNTFTCSVLHEGLH

NHHTEKSLSHSPGK

The antibody of the present embodiment may be a chimeric antibody having variable regions respectively of SEQ ID NOs: 18 and 19. The term "chimeric antibody" as used herein refers to an antibody in which variable regions of an antibody originated from a specific species and constant regions of an antibody originated from a species heterogeneous to the antibody are linked to one another. The antibody of the present embodiment may be a humanized antibody which has light chain CDR1, CDR2 and CDR3 respectively consisting of the amino acid sequences of SEQ ID NOs: 12, 13 and 14; and heavy chain CDR1, CDR2 and CDR3 respectively consisting of the amino acid sequences of SEQ ID NOs: 15, 16 and 17. The term "humanized antibody" as used herein refers to an antibody produced by grafting gene sequences for CDRs of an antibody originated from a non-human animal into a gene for a human antibody (CDR grafting).

The antibody of the present embodiment includes, within the scope thereof, an antibody for which the amino acid sequence is modified without decreasing its activity to bind to a human TGF-β1 LAP-D. Examples of the modification of the amino acid sequence include the substitution, deletion, addition and/or insertion of an amino acid residue. The modification site in the amino acid sequence for the antibody may be a constant region or a variable region of a heavy chain or a light chain. In the case where it is intended to modify a variable region, it is preferred to modify a framework region (FR). The term "FR" refers to a region which occurs in a variable region of each of light chains and heavy chains of an antibody and is other than CDRs. An FR plays a roll of a scaffold for linking three CDRs to one another and contributes to the stabilization of the structures of the CDRs. The modification of the amino acid sequence for the antibody can be carried out by introducing a mutation into a gene for the antibody by a known method such as a DNA recombination technique and other molecular biological techniques.

The number of amino acid residues to be modified is generally 10 or less, preferably 5 or less, more preferably 3 or less. The modification of the amino acid sequence for the antibody is preferably conservative substitution. The term "conservative substitution" as used herein refers to the substitution of an amino acid residue with an amino acid residue that has a side chain having the same chemical property as that of a side chain of the aforementioned amino acid residue. The conservative substitution of an amino acid sequence is known in the art. Alternatively, the amino acid sequence for the antibody may be modified by the method disclosed in U.S. Patent Application Publication No. 2018/0179298 and comprises modifying an amino acid residue in FR3 in the antibody and can control the affinity of the antibody for an antigen.

The antibody of the present embodiment may be modified with a labeling substance that is known in the art. The labeling substance is not particularly limited, as long as a detectable signal can be generated. For example, the labeling substance may be a substance which can generate a signal by itself (wherein the substance is also referred to a "signal generating substance", hereinafter), or may be a substance which can catalyze the reaction with another substance to generate a signal. Examples of the signal generating substance include a fluorescent substance and a radioactive isotope. An example of the substance capable of catalyzing the reaction with another substance to generate a detectable signal is an enzyme. Examples of the enzyme include alkaline phosphatase, peroxidase, β-galactosidase, and luciferase. Examples of the fluorescent substance include: a fluorescent dye such as fluorescein isothiocyanate (FITC), rhodamine and Alexa Fluor (registered trademark); and a fluorescent protein such as green fluorescent protein (GFP). Examples of the radioactive isotope include $^{125}$I, $^{14}$C and $^{32}$P.

Another embodiment includes an isolated and purified polynucleotide encoding the antibody of the present embodiment or a fragment thereof. Still another embodiment includes a vector carrying the polynucleotide. The vector is a polynucleotide construct that is designed for transduction or transfection. The type of the vector is not particularly limited, and can be selected appropriately from vectors known in the art, such as an expression vector, a cloning vector and a viral vector. Still another embodiment includes a host cell harboring the vector. The type of the host cell is not particularly limited, and can be selected appropriately from a eukaryotic cell, a prokaryotic cell and a mammal cell.

The antibody of the present embodiment can be produced by a known monoclonal antibody production method such as a hybridoma method and a phage display method. In the case where it is intended to produce a hybridoma capable of producing the antibody of the present embodiment by a hybridoma method, a polypeptide comprising a part or the whole of the amino acid sequence for TGF-β1-LAP can be used as an immunogen. It is preferred that the polypeptide includes an integrin binding site of LAP-D. A specific example of the polypeptide is TGF-β1-LAP (amino acid residues at position-30 to position-390). The polypeptide may have a mutation at a cutting site located between the amino acid sequence for activated TGF-β and the amino acid sequence for LAP, for the purpose of avoiding the cutting of the polypeptide with a protease. For example, when the amino acid residue arginine at position-278 is substituted with a non-arginine amino acid residue such as alanine in the polypeptide, the polypeptide cannot be recognized by a protease and therefore cannot be cut with the protease. The method for synthesizing the polypeptide is known, and an example of the method is a Fmoc solid-phase synthesis method. Because the synthesized polypeptide has poor immunogenicity, it is preferred to link the polypeptide to a carrier protein such as keyhole limpet hemocyanin (KLH) and albumin. In the case where the carrier protein and the synthesized peptide are linked to each other by crosslinking, it is preferred to add a cysteine residue to the N-terminal or the C-terminal of the sequence for the polypeptide in the synthesis of the polypeptide. Alternatively, the immunogen may be produced in the form of a recombinant protein. Recombinant TGF-β can be produced by inserting a polynucleotide encoding the amino acid sequence for TGF-β into a known expression vector, then transforming a host cell with the vector to express the recombinant TGF-β, and then purifying the recombinant TGF-β by a known method. The purified recombinant TGF-β can be used as an immunogen.

Subsequently, a proper animal (e.g., mouse, rat, hamster, rabbit) is immunized with the polypeptide thus produced, and an antibody-producing cell such as a spleen cell is obtained from the immunized animal. The antibody-producing cell thus obtained is fused to a proper myeloma cell by a known hybridoma production method such as a method disclosed in Kohler and Milstein, Nature, vol. 256, p. 495-497, 1975, thereby producing a hybridoma. For the screening of the hybridoma, a synthesized polypeptide that is used as the immunogen can be used. The antibody of the present embodiment can be obtained from a culture supernatant of the hybridoma or an ascitic fluid from a mammal who has received the intraperitoneal administered of the hybridoma. The antibody thus obtained may be purified by a known method such as salting out, affinity chromatography and gel filtration.

When a phage display method is employed, a Fab fragment of the antibody of the present embodiment can be produced, for example. Firstly, an animal such as mouse is immunized with the synthesized polypeptide, then mRNA is obtained from the spleen of the animal, and then cDNA is synthesized using the mRNA. The cDNA thus obtained is amplified using a known primer for cloning an antibody gene to produce a Fab phage library. A Fab clone of the antibody of the present embodiment can be produced using the library by a Fab phage display method and biopanning (see Philippa M. O'Brien and Robert Aitken, Antibody Phage Display, (2002) Methods in Molecular Biology Volume No. 178) that are known.

In the case where there is a hybridoma capable of producing the antibody of the present embodiment, the amino acid sequence for the antibody of the present embodiment can be analyzed in the manner mentioned in Example 3 below. Firstly, a polynucleotide encoding the antibody of the present embodiment is synthesized using RNA extracted from the hybridoma by a reverse transcription reaction and a Rapid Amplification of cDNA ends (RACE) method. Subsequently, the nucleotide sequence for the synthesized polynucleotide is analyzing by sequencing, and the amino acid sequence for the antibody is determined on the basis of the nucleotide sequence.

As demonstrated in Examples mentioned below, when the antibody of the present embodiment is used in a sandwich ELISA method, it becomes possible to achieve a high-detectability measurement of a recombinant LAP-D as well as a LAP-D in a biological sample (e.g., plasma) collected from a subject. Therefore, the antibody of the present embodiment is useful for the measurement of a LAP-D in a biological sample. In recent years, it is found that the PLK-induced activation and release of TGF-β can accelerate liver fibrosis. It is considered that a LAP-D produced by the cut out of LAP with PLK is released in blood. Therefore, the antibody of the present embodiment is useful for, for example, the study for elucidating the relationship between the blood level of a LAP-D and the progression of liver fibrosis.

[2. Reagent for Detecting LAP Degradate]

The reagent for detecting a LAP degradate of the present embodiment (also simply referred to as a "reagent", hereinafter) is a reagent comprising an isolated monoclonal antibody against a human TGF-β LAP degradate of the above-mentioned embodiment.

As mentioned above, the antibody of the present embodiment exhibits high LAP-D detectability when used in a sandwich ELISA method, and therefore the reagent of the present embodiment can be used suitably in a sandwich ELISA method. In the reagent of the present embodiment, the antibody may be modified with a labeling substance that is known in the art. The details about the labeling substance are the same as those mentioned with respect to the antibody of the present embodiment.

The form of the reagent of the present embodiment is not particularly limited, and may be a solid form (e.g., a powder, a crystal, a freeze-dried product) or a liquid form (e.g., a solution, a suspension, an emulsion). In the case where the reagent has a liquid form, the solvent to be used is not particularly limited, as long as the antibody of the present embodiment can be dissolved and stored in the solvent. Examples of the solvent include water, physiological saline, phosphate-buffered saline (PBS), tris-buffered saline (TBS) and Good's buffer. Specific examples of the Good's buffer include MES, Bis-Tris, ADA, PIPES, Bis-Tris-Propane, ACES, MOPS, MOPSO, BES, TES, HEPES, HEPPS, Tricine, Tris, Bicine and TAPS.

The reagent of the present embodiment may contain a known additive. Examples of the additive include: a protein stabilizer such as bovine serum albumin (BSA); a preservative agent such as sodium azide; and an inorganic salt such as sodium chloride.

Figure 2:
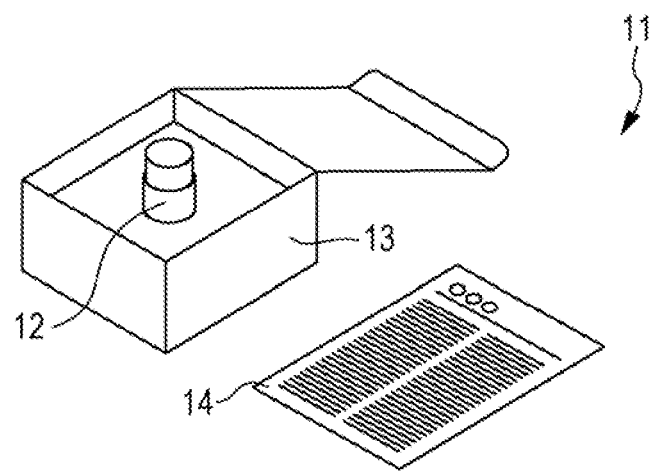
FIG. 2 is a diagrammatic illustration showing one example of the reagent of the present embodiment.

In the present embodiment, it is possible to pack a container including the reagent therein in a box and to provide the box to a user. In the box, a package insert may also be included. On the package insert, the composition, the instruction of usage, the storage method and the like of the reagent of the present embodiment may be written. One example of the reagent of the present embodiment is shown in FIG. 2. In FIG. 2, 11 represents the reagent of the present embodiment, 12 represents a first container in which the antibody of the present embodiment is enclosed, 13 represents a package box, and 14 represents a package insert.

[3. Reagent Kit for Detecting LAP Degradate]

The reagent kit for detecting a LAP degradate of the present embodiment (also simply referred to as "reagent kit", hereinafter) is a reagent kit comprising: a first reagent which contains the above-mentioned isolated monoclonal antibody against a human TGF-β LAP degradate according to the present invention; and a second reagent which contains an antibody specifically recognizing a region comprising a leucine residue at the N-terminal of the amino acid sequence of SEQ ID NO: 3.

The amino acid sequence of SEQ ID NO: 3 is the amino acid sequence for a LAP-D produced by the cutting out of human TGF-β1 LAP with PLK (i.e., a sequence composed of amino acid residues at position-59 to position-278 in the amino acid sequence of SEQ ID NO: 1). The N-terminal leucine residue in this amino acid sequence is a cutting site of LAP with PLK. Namely, the antibody in the second reagent is an antibody specifically recognizing a cut face of LAP with PLK. The antibody itself is known, and is disclosed in U.S. Patent Application Publication No. 2011/0071278 (wherein U.S. Patent Application Publication No. 2011/0071278 is incorporated by reference herein). In a preferred embodiment, the antibody in the second reagent is an antibody specifically recognizing a region comprising a leucine residue at the N-terminal of the amino acid sequence of SEQ ID NO: 22. The amino acid sequence of SEQ ID NO: 22 is a sequence composed of amino acid residues at position-59 to position-68 in the amino acid sequence of SEQ ID NO: 1.

In the present embodiment, each of the reagents may contain a known additive. The details about the additive are the same as those mentioned with respect to the reagent of the present embodiment. The form of the antibody in each of the reagents is not particularly limited, and may be a solid form (e.g., a powder, a crystal, a freeze-dried product) or a liquid form (e.g., a solution, a suspension, an emulsion).

The reagent kit of the present embodiment can be used suitably in a sandwich ELISA method. In the reagent kit of the present embodiment, it is preferred that the antibody of the present embodiment which is contained in the first reagent is used as a detection antibody in a sandwich ELISA method. It is preferred that the antibody contained in the second reagent is used as a capture antibody in a sandwich ELISA method. The term "detection antibody" as used herein refers to an antibody which can bind specifically to a substance to be tested, and which can provide a detectable signal through a labeling substance when the antibody is bound to the labeling substance. It is preferred for the detection antibody is not immobilized on a solid phase. The term "capture antibody" as used herein refers to an antibody which can specifically bind to a substance to be tested that is the analyte and can be immobilized on a solid phase to capture the substance to be tested onto the solid phase.

The reagent kit of the present embodiment may further include a solid phase on which the capture antibody is to be immobilized. The solid phase may be an insoluble support on which the capture antibody can be immobilized. The mode of the immobilization of the capture antibody on the solid phase is not particularly limited. For example, the capture antibody and the solid phase may bind directly or may bind indirectly with another substance intercalated therebetween. An example of the direct binding is physical adsorption. An example of the indirect binding is a binding through a combination of a biotin-type compound (including biotin and a biotin analog such as desthiobiotin) and an avidin-type compound (including avidin and an avidin analog such as streptavidin and Tamavidin (registered trademark)). In this case, by modifying the capture antibody with a biotin-type compound in advance and binding an avidin-type compound to the solid phase in advance, the capture antibody and the solid phase can bind to each other indirectly through the binding between the biotin-type compound and the avidin-type compound.

The material for the solid phase is not particularly limited, and can be selected from, for example, an organic polymeric compound, an inorganic compound, a biological polymer and others. Examples of the organic polymeric compound include latex, polystyrene and polypropylene. Examples of the inorganic compound include a magnetic material (e.g., iron oxide, chromium oxide, ferrite), silica, alumina and a glass. Examples of the biological polymer include insoluble agarose, insoluble dextran, gelatin and cellulose. It is possible to use two or more of these substances in combination. The form of the solid phase is not particularly limited, and examples of the form include a micro plate, a micro tube, a test tube, a particle and a film. Among these forms, a micro plate and a particle (particularly a magnetic particle) is preferred.

In the present embodiment, the antibody to be contained in each of the reagents may be modified with a labeling substance that is known in the art. It is particularly preferred that the antibody to be contained in the first reagent is modified with a labeling substance. The details about the labeling substance are the same as those mentioned with respect to the antibody of the present embodiment. In the case where the labeling substance is an enzyme, the reagent kit may include a substrate for the enzyme. The substrate can be selected appropriately depending on the type of the enzyme.

Figure 3:
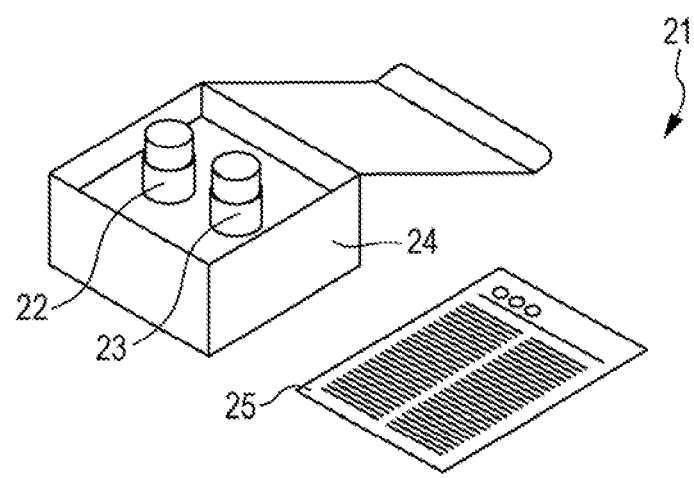
FIG. 3 is a diagrammatic illustration showing one example of the reagent kit of the present embodiment.
Figure 4A:
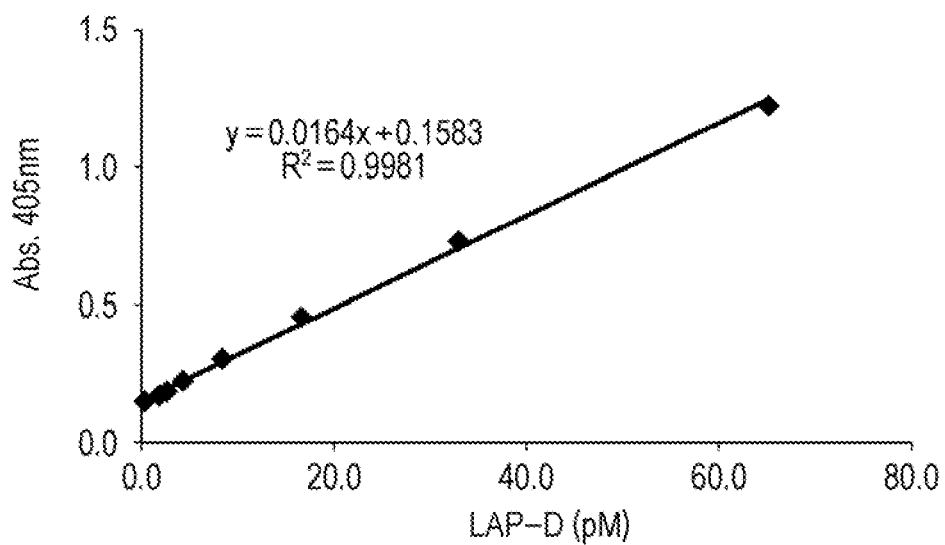
FIG. 4A shows a calibration curve produced by measuring a dilution series of a LAP-D using the isolated monoclonal antibody of the present embodiment as a detection antibody.
Figure 4B:
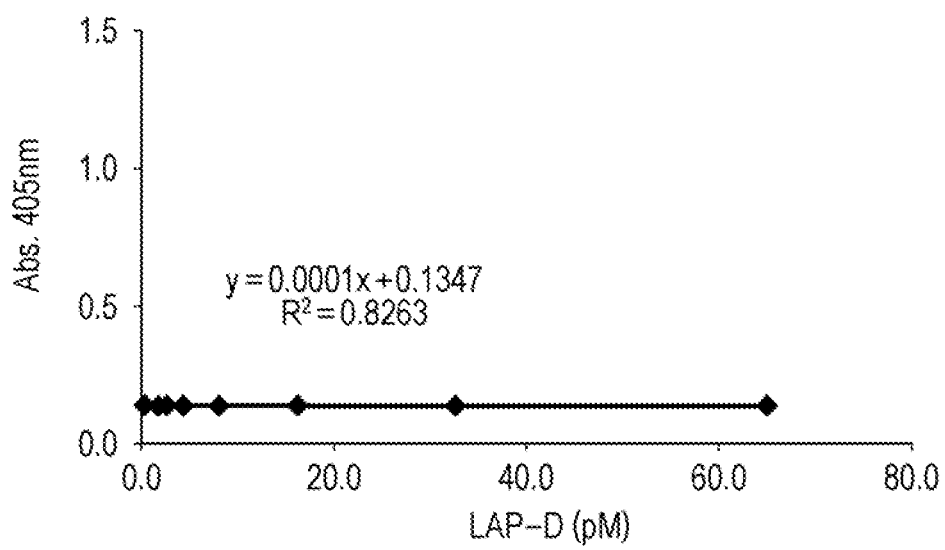
FIG. 4B shows a calibration curve produced by measuring a dilution series of a LAP-D using a commercially available anti-LAP antibody (141402, manufactured by BioLegend) as a detection antibody.
Figure 4C:
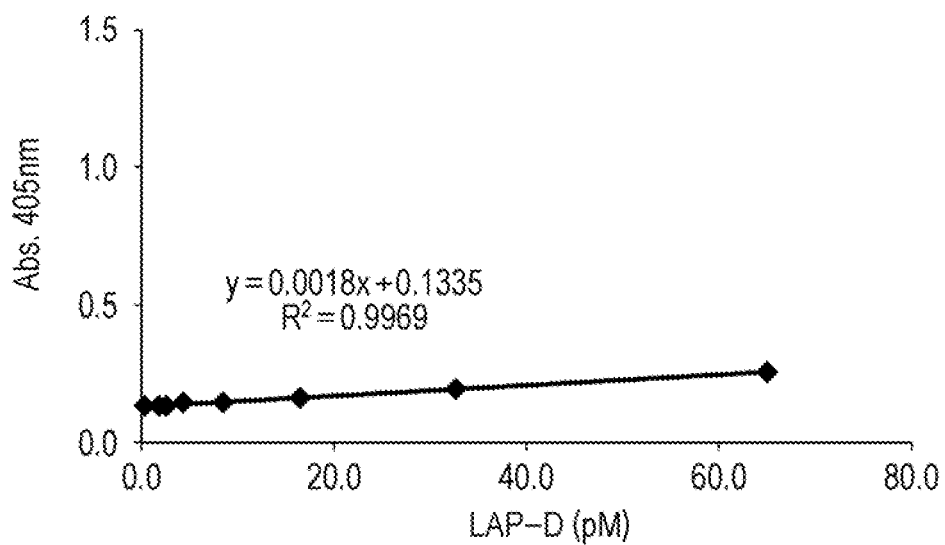
FIG. 4C shows a calibration curve produced by measuring a dilution series of a LAP-D using a commercially available anti-LAP antibody (349702, manufactured by BioLegend) as a detection antibody.
Figure 4D:
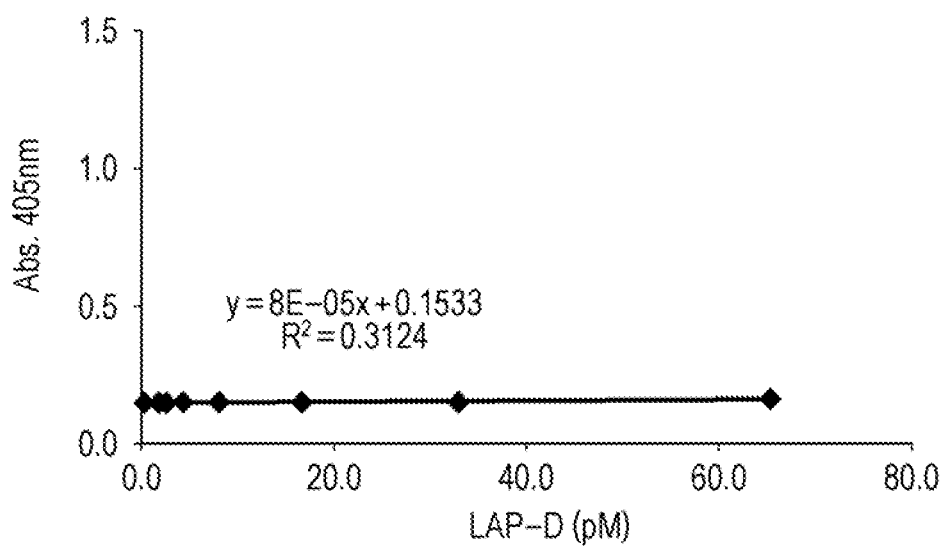
FIG. 4D shows a calibration curve produced by measuring a dilution series of a LAP-D using a commercially available anti-LAP antibody (MA5-17186, manufactured by Thermo Fisher Scientific) as a detection antibody.

In the present embodiment, it is possible to pack containers respectively including the first and second reagents in a box and provide the box to a user. In the box, a package insert may also be included. On the package insert, the constitution, the instruction of usage, the storage method and the like of the reagent kit of the present embodiment may be written. One example of the reagent kit of the present embodiment is shown in FIG. 3. In FIG. 3, 21 represents the reagent kit of the present embodiment, 22 represents a first container in which the antibody of the present embodiment is enclosed, 23 represents a second container in which the capture antibody of the present embodiment is enclosed, 24 represents a package box, and 25 represents a package insert. In this example, the reagent kit may further include a solid phase on which the capture antibody is to be immobilized.

In the present embodiment, the reagent kit may include a calibrator for a LAP-D. One example of the calibrator is a calibrator for LAP-D quantification use. For example, this calibrator may be provided with a buffer solution containing no LAP-D (i.e., negative control) and a buffer solution containing a LAP-D at a known concentration. The LAP-D to be contained in the calibrator may be a recombinant LAP-D or a synthetic peptide consisting of the amino acid sequence for a LAP-D. The recombinant LAP-D can be produced by the limited proteolysis of a recombinant human TGF-β LAP protein with a protease such as PLK.

[4. Method for Measuring Human TGF-β LAP Degradate]

The method for measuring a human TGF-β LAP degradate (also simply referred to as "measurement method", hereinafter) of the present embodiment includes measuring a human TGF-β LAP degradate in a biological sample collected from a subject using the antibody.

The subject is not particularly limited, and an example of the subject is a patient who carries a clinical condition or disease associated with the abnormality in TGF-β. An example of the clinical condition is the fibrosis of liver, lung, kidney or the like. Examples of the disease include viral hepatitis (particularly hepatitis C), hepatic cirrhosis and cancer. An example of the biological sample is a clinical specimen collected from a subject. Examples of the clinical specimen include blood (whole blood, plasma, serum), a tissue fluid, a cerebrospinal fluid, an ascitic fluid and urine.

In the case where insoluble contaminants such as cells are contained in the biological sample, the contaminants may be removed from the biological sample by a known means such as centrifugation and filtration. The biological sample may be diluted with a proper water-based medium, if necessary. The water-based medium is not particularly limited, as long as the below-mentioned measurements are not interfered. Examples of the water-based medium include water, physiological saline and a buffer solution. The buffer solution is not particularly limited, as long as the buffer solution can exhibit a buffering activity at an almost neutral pH value (e.g., a pH value of 6 to 8 inclusive). Examples of the buffer solution include: Good's buffer such as HEPES, MES and PIPES; TBS; and PBS.

The wording "measure a human TGF-β LAP degradate" as used herein includes the determination of the value of the quantity or concentration of a human TGF-β LAP-D and the acquisition of information that reflects the quantity or concentration of a human TGF-β LAP-D. The term "information that reflects the quantity or concentration of a human TGF-β LAP-D" as used herein refers to an indicator that varies depending on the quantity or concentration of a human TGF-β LAP-D in a biological sample or a measurement sample prepared from the biological sample. The indicator is preferably an indicator for a visibly-detectable or mechanically-measurable optical change. Examples of the indicator for the optical change include an emission intensity, a fluorescence intensity, an absorbance, a turbidity and a color optical density.

The method for measuring a LAP-D using the antibody of the present embodiment is not particularly limited, and can be selected appropriately from the known immunological measurement methods. Examples of the measurement method include an ELISA method and a western blot method. Alternatively, the immune complex transfer immunoassay disclosed in Japanese Laid-Open Patent Publication No. 1-254868 may also be employed. Among these methods, an ELISA method is preferred. The type of the ELISA method may be anyone selected from a sandwich method, a competition method, a direct method, an indirect method and the like, and a sandwich method is particularly preferred. As one example, a case where the measurement is carried out by a sandwich ELISA method will be described hereinbelow. In this example, the antibody of the present embodiment is used as a detection antibody.

Firstly, a complex comprising a LAP-D, a capture antibody against the LAP-D, and the antibody of the present embodiment (i.e., detection antibody) is formed on a solid phase. The complex can be formed by mixing a biological sample that may contain a biomarker, the capture antibody and the detection antibody together. The solution containing the complex is contacted with a solid phase on which the capture antibody can be captured, thereby forming the complex on the solid phase. Alternatively, it is also possible to use a solid phase having a capture antibody immobilized previously thereon. Namely, a solid phase having a capture antibody immobilized thereon, a biological sample and a detection antibody may contact together to form the complex on the solid phase.

The capture antibody is not particularly limited, as long as the capture antibody can bind specifically to a LAP-D. In the case where the capture antibody is a monoclonal antibody, it is preferred that the epitope of the capture antibody is a site different from an integrin binding site. In a preferred embodiment, the capture antibody is an antibody capable of recognizing specifically a region comprising a leucine residue located at the N-terminal of the amino acid sequence of SEQ ID NO: 3. More preferably, the capture antibody is an antibody capable of recognizing specifically a region comprising a leucine residue located at the N-terminal of the amino acid sequence of SEQ ID NO: 22.

A biomarker contained in the biological sample can be measured by detecting the complex formed on the solid phase by a method known in the art. For example, in the case where the antibody of the present embodiment which is labeled with a labeling substance is used as a detection antibody, the human TGF-β1 LAP-D in the biological sample can be measured by detecting a signal generated from the labeling substance. Alternatively, in the case where a labeling secondary antibody against the detection antibody is used, the human TGF-β1 LAP-D in the biological sample can also be measured in the same manner. The details about the labeling substance are the same as those mentioned with respect to the antibody of the present embodiment.

In the present embodiment, it is also possible to carry out a B/F (Bound/Free) separation procedure for removing an unreacted free component that is not involved in the formation of the complex between the formation of the complex and the detection of the complex. The term "unreacted free component" as used herein refers to a component which is not involved in the formation of the complex. Examples of the unreacted free component include a capture antibody and a detection antibody each of which does not bind to a human TGF-β1 LAP-D. The means for the B/F separation is not particularly limited. In the case where the solid phase comprises particles, the B/F separation can be achieved by collecting only the complex-captured solid phase by centrifugation. In the case where the solid phase is a container such as a micro plate and a micro tube, the B/F separation can be achieved by removing a solution containing the unreacted free component. In the case where the solid phase comprises magnetic particles, the B/F separation can be achieved by removing a solution containing the unreacted free component by suction using a nozzle while magnetically constraining the magnetic particles with a magnet. This is preferred from the viewpoint of automatization. Subsequent to the removal of the unreacted free component, the solid phase having the complex immobilized thereon may be washed with a proper water-based medium such as PBS.

The wording "detect a signal" as used herein includes, within the scope thereof, the detection of the presence or absence of a signal, the quantification of the intensity of a signal, and the semi-quantitative detection of the intensity of a signal. The term "semi-quantitative detection" as used herein refers to the matter that the level of the intensity of a signal is rated in stages, such as "no signal is observed", signal is weak", "signal is moderate" and "signal is intense". In the present embodiment, it is preferred to detect the intensity of a signal quantitatively or semi-quantitatively.

The method for measuring the signal is known in the art. In the present embodiment, the measurement method may be selected appropriately depending on the type of the signal coming from the labeling substance. For example, in the case where the labeling substance is an enzyme, it is possible to measure a signal, e.g., light and color, generated upon the reaction of the enzyme with a substrate for the enzyme using a known device such as a spectrophotometer.

The substrate for the enzyme can be selected appropriately from known substrates depending on the type of the enzyme to be used. For example, in the case where alkaline phosphatase is used as the enzyme, examples of the substrate for the enzyme include: a chemiluminescent substrate such as CDP-Star (registered trademark) (disodium 4-chloro-3-(methoxyspiro[1,2-dioxetane-3,2'-(5'-chloro)tricyclo [3.3.1.13,7]decan]-4-yl)phenylphosphate) and CSPD (registered trademark) (disodium 3-(4-methoxyspiro[1,2-dioxetane-3,2-(5'-chloro)tricyclo[3.3.1.13,7]decan]-4-yl) phenylphosphate); and a luminescent substrate such as 5-bromo-4-chloro-3-indolyl phosphoric acid (BCIP), disodium 5-bromo-6-chloro-indolylphosphate and p-nitrophenylphosphoric acid. In the case where peroxidase is used as the enzyme, examples of the substrate include: a chemiluminescent substrate such as luminol and a derivative thereof; and a chromogenic substrate such as 2,2'-azinobis(3-ethyl-benzothiazoline-6-sulfonic acid ammonium salt) (ABTS), 1,2-phenylenediamine (OPD) and 3,3',5,5'-tetramethylbenzidine (TMB).

In the case where the labeling substance is a radioactive isotope, radioactive ray that is a signal can be measured using a known device such as a scintillation counter. In the case where the labeling substance is a fluorescent substance, fluorescent light that is a signal can be measured using a known device such as a fluorescence microplate reader. An excitation wavelength and a fluorescence wavelength can be determined appropriately depending on the type of the fluorescent substance to be used.

The result of the detection of the signal can be employed as the result of the measurement of a human TGF-β1 LAP-D. For example, in the case where it is intended to quantify the intensity of a signal, a measurement value of the signal intensity or a value acquired from the measurement value can be employed as a measurement result for the human TGF-β1 LAP-D. An example of the value acquired from a measurement value of the signal intensity is a value determined by subtracting a measurement value of a negative control sample or a background value from the measurement value. It is also possible to assign the measurement value of the signal intensity to a calibration curve to determine the value of the quantity or concentration of the human TGF-β1 LAP-D. The negative control sample can be selected appropriately, and an example of the negative control sample is a biological sample collected from a normal person.

In the present embodiment, a human TGF-β1 LAP-D in a biological sample may be measured by a sandwich ELISA method using a capture antibody immobilized on magnetic particles and the antibody of the present embodiment (detection antibody) labeled with a labeling substance. In this case, the measurement may be carried out using a commercially available automated immunoassay device such as HISCL series systems (manufactured by Sysmex corporation).

[5. Method for Monitoring Measurement Value of Human TGF-β LAP Degradate]

In the method for monitoring a measurement value of a human TGF-β LAP degradate according to the present embodiment (wherein the method is also simply referred to as "monitoring method", hereinafter), a step of measuring a TGF-β LAP-D in a first biological sample collected from a subject using the antibody of the present embodiment and a step of measuring the TGF-β LAP-D in a second biological sample collected from the subject. The first biological sample is a biological sample collected from a subject at a first point of time. The second biological sample is a biological sample collected from the same subject at a second point of time that is different from the first point of time. In the monitoring method of the present embodiment, the change in the measurement value of LAP degradate in a subject can be monitored by comparing the measurement values for a TGF-β LAP degradate in the first and second biological samples with each other.

An example of each of the first and second biological samples is a clinical specimen collected from a subject. The details about the clinical specimen are the same as those mentioned with respect to the measurement method of the present embodiment. It is preferred that the first biological sample and the second biological sample are of the same type. The subject is not particularly limited, and an example of the subject is a patient who carries a clinical condition or disease associated with the abnormality in TGF-β. The details about the clinical condition and the disease are the same as those mentioned with respect to the measurement method of the present embodiment. Alternatively, the subject may be a patient who has received a treatment for a clinical condition or disease associated with the abnormality of TGF-β or a patient who is scheduled to receive the treatment.

The first point of time is not particularly limited, and may be an arbitrary point of time. The second point of time is not particularly limited, as long as the second point of time is different from the first point of time. The second point of time may be a point of time at which a period selected from the range of 1 day to 6 months has passed since the first point of time. More specifically, the period between the first point of time and the second point of time may be about 3 months. For example, it is possible to collect a biological sample from a subject and measure the biological sample every about 3 months. In the case where the subject has received a treatment for a clinical condition or disease associated with the abnormality in TGF-β, it is possible to employ a point of time at which the subject receives the treatment as the first point of time and employ a point of time at which the subject receives next treatment as the second point of time. In the case where the subject is a patient who is scheduled to receive a treatment for a clinical condition or disease associated with the abnormality in TGF-β, it is possible to employ a point of time before the start of the treatment or the point of time of the start of the treatment as the first point of time and employ a point of time at which a predetermined period has passed since the start of the treatment as the second point of time. In the case where the clinical condition or disease associated with the abnormality in TGF-β closely relates to a measurement value for a TGF-β LAP degradate, the efficacy of the treatment can be monitored by comparing the measurement values for the TGF-β LAP degradate in the first and second biological samples with each other.

The details about the method for measuring a TGF-β LAP-D in each of the first and second biological samples are the same as those mentioned with respect to the measurement method of the present embodiment. The measurement of the first biological sample and the measurement of the second biological sample may be carried out substantially simultaneously or sequentially. In the case where the first biological sample and the second biological sample are measured substantially simultaneously, it is preferred to store the first biological sample properly until the measurement is started. If necessary, the second biological sample may also be stored properly until the measurement is started.

Hereinafter, the present invention will be described in more detail with reference to examples. However, the present invention is not limited to these examples.

EXAMPLES

[Production Example] Production of Monoclonal Antibody Capable of Recognizing Integrin Binding Site of Human TGF-β LAP Degradate (1) Production of Antigen A polypeptide having a mutation R278A inserted to TGF-β1-LAP (amino acid residues at position-30 to position-390) was produced. A polynucleotide, which had a sequence in which a His tag was added to a gene sequence encoding the polypeptide, was linked to the downstream of Igk signal, and the resultant polynucleotide was expressed in a HEK293F cell using a pOrip vector. A TGF-β1-LAP was purified from a soluble fraction using HISTRAP (manufactured by GE healthcare) in accordance with the manufacturer's written usage instructions. The His tag was cut out with TEV protease, and the resultant TGF-β1-LAP was loaded onto the HISTRAP column again, and a fraction passing through the column was collected. The fraction was purified by a known method using a gel filtration column (SUPERDEX 200 Increase 10/300 GL, manufactured by GE Healthcare), and a low-molecular-weight fraction was collected. The low-molecular-weight fraction thus collected was used as an antigen.

(2) Production and Screening of Hybridoma

A female Balb/c mouse was immunized with the antigen, and a hybridoma capable of producing an antibody against a human TGF-β LAP degradate is produced by the method disclosed in Kohler and Milstein, Nature, vol. 256, p. 495-497, 1975. With respect to the hybridoma thus produced, a cell line capable of producing an antibody exhibiting reactivity to the antigen was selected by an ELISA method. The selected hybridoma was cloned by a limiting dilution method to further select a cell line capable of producing an antibody against the human TGF-β LAP degradate stably.

(3) Purification of Monoclonal Antibody

A culture supernatant of the hybridoma (100 mL) was filtrated through a 0.22-μm filter to remove insoluble matters. A filtrated culture supernatant was passed through a column having 1 mL of Protein G SEPHAROSE 4B (manufactured by GE Healthcare) packed therein to adsorb the antibody onto the column. A non-specific adsorption matter is removed from the column, and then the column was placed under an acidic condition to liberate a monoclonal antibody. The collected monoclonal antibody was dialyzed with 100-fold volume of phosphate-buffered saline (PBS) to produce a purified monoclonal antibody. The monoclonal antibody thus produced was also called an "anti-LAP-D antibody (A10)" hereinafter, and was used in the following examples.

[Example 1] Comparison Between Anti-LAP-D Antibody (A10) and Commercially Available Anti-LAP Antibody In order to evaluate the sensitivity of a sandwich ELISA method using the anti-LAP-D antibody (A10) as a detection antibody, a comparison test between the anti-LAP-D antibody (A10) and three commercially available anti-LAP antibodies was carried out.

(1) Conditions for Test (1.1) Preparation of Detection Antibodies

Each of the anti-LAP-D antibody (A10), an anti-LAP antibody (141402, manufactured by BioLegend), an anti-LAP antibody (349702, manufactured by BioLegend) and an anti-LAP antibody (MA5-17186, manufactured by Thermo Fisher Scientific) was labeled with biotin using Biotin Labeling Kit-NH$_2$ (Cat #LK03, manufactured by Dojindo Molecular Technologies, Inc.) to produce a detection antibody. Each of the detection antibodies thus produced was diluted with an antibody dilution solution (HEPES containing 10 μg/mL of mouse IgG) to produce a solution of each of the detection antibodies (5 μg/mL each).

(1.2) Preparation of Calibration Curve Standard Substance (LAP-D)

Human recombinant LAP (20 μg/mL, manufactured by R&D) (7.0 μL), PLK (59.3 μg/mL, manufactured by Sigma-Aldrich) (9.4 μL) and PBS (83.6 μL) were mixed together, and the resultant mixed solution was incubated at 37° C. for 1 hour to obtain a LAP-D solution. The molecular weight of LAP was determined as 27 kDa, and the concentration of the LAP-D solution was 52 nM. The LAP-D solution was diluted 800 folds with 1% BSA/TBS, and the upper limit of a calibration curve was preset to 65 pM. The diluted LAP-D solution was further diluted to prepare a dilution series (32.5 pM, 16.3 pM, 8.1 pM, 4.1 pM, 2.0 pM, 1.0 pM and 0 pM).

(1.3) Preparation of Capture Antibody

As a capture antibody, an antibody against a LAP-D, which is disclosed in U.S. Patent Application Publication No. 2011/0071278 (also referred to as "anti-L59 LAP-D antibody", hereinafter) was used. The antibody recognizes specifically a cut face of LAP that is cut with PLK, i.e., a region comprising a leucine residue located at the N-terminal of the amino acid sequence of SEQ ID NO: 3. The anti-L59 LAP-D antibody was diluted with TBS to produce a capture antibody solution (20 μg/mL).

(2) Test Method

The capture antibody solution was dispensed in a plate in which six NN modules "F8 MAXISORP" (manufactured by NUNC) were set in one frame at a volume of 50 μL per well, and the plate was incubated at 4° C. overnight. The plate was washed three times with a wash solution (TBS containing 0.05% of TWEEN20) at a volume of 200 μL per well. A blocking solution (TBS containing 1% of BSA) was dispensed at a volume of 350 μL per well, and the plate was incubated at 4° C. overnight. The blocking solution was removed, and a calibration curve standard substance which was diluted to eight different levels was dispensed at a volume of 50 μL per well (n=3), and the plate was incubated at 4° C. overnight. The plate was washed three times with the wash solution as mentioned above, then the solution of each of the detection antibodies was dispensed at a volume of 50 μL per well, and then the plate was incubated at 4° C. for three hours. The plate was washed three times with the wash solution as mentioned above, then an alkaline phosphatase-streptavidin solution (0.05 μg/mL) was dispensed at a volume of 50 μL per well, and then the plate was incubated at room temperature for three hours. The plate was washed three times with the wash solution as mentioned above, then a chromogenic substrate solution (4-nitrophenylphosphate) was dispensed at a volume of 100 μL per well, and then the plate was incubated at 4° C. overnight. The plate was warmed to room temperature, and then an absorbance at 405 nm was measured. The absorbance measurement values were plotted against the LAP-D concentrations of the calibration curve standard substance to produce a calibration curve.

(3) Results

The calibration curves for the detection antibodies are shown in FIGS. 4A to 4D, respectively. As apparent from these drawings, a calibration curve showing quantitativeness was produced only when the anti-LAP-D antibody (A10) was used as a detection antibody. It was demonstrated that the anti-LAP-D antibody (A10) had high sensitivity to a LAP-D produced using PLK and was useful as a detection antibody for an ELISA method for detecting a LAP-D.

[Example 2] Evaluation of Usefulness of Anti-LAP-D Antibody (A10)

In order to evaluate the usefulness of the anti-LAP-D antibody (A10), a LAP-D in a human plasma specimen was measured by employing an ELISA method. For comparison, the measurement of an anti-LAP-D antibody in a commercially available LAP-D detection ELISA kit was carried out under the same conditions.

(1) Conditions for Test (1.1) Biological Samples

Blood was collected several multiple times at certain intervals from each of six patients who had been infected with hepatitis C virus and had received the administration of a direct-acting antiviral agent (DAA) to obtain plasma specimens (48 specimens). Each of the plasma specimens was diluted 20-fold with a blocking solution (TBS containing 1% of BSA) and was then used for the measurement. With respect to these plasma specimens, a LAP-D was measured in advance using a commercially available LAP-D detection ELISA kit (manufactured by R&D Systems), and specimens for which the measurement was impossible and specimens which showed very small measurement values were selected. The measurement was carried out in accordance with the manual included in the kit. In Example 2, the selected specimens were used.

(1.2) Detection Antibody, Capture Antibody and Calibration Curve Standard Substance As a detection antibody, a biotin-labeled anti-LAP-D antibody (A10) which was prepared in the same manner as in Example 1 was used. As a detection antibody for comparison purpose, a biotin-labeled anti-human LAP TGF-β1 antibody (BAM2462, manufactured by R&D Systems) (also referred to as an "BAM2462 antibody", hereinafter) in the above-mentioned LAP-D detection ELISA kit was used. Each of the detection antibodies was diluted with an antibody dilution solution (HEPES containing 10 μg/mL of mouse IgG) to produce a solution of each of the detection antibodies (2.5 μg/mL each). A calibration curve standard substance and a capture antibody were prepared in the same manner as in Example 1.

(2) Test Method

The capture antibody solution was dispensed in plates in which eight NN modules "F8 MAXISORP" (manufactured by NUNC) were set in four frames (two plates×two types of antibodies) at a volume of 50 μL per well, and the plates were incubated at 4° C. overnight. The plates were washed and blocked in the same manner as in Example 1. The blocking solution was removed, and each of the calibration curve standard substance which was diluted to eight different levels and a 20-fold-diluted plasma specimen was dispended at a volume of 50 μL per well (n=3), and the plates were incubated at 4° C. overnight. The plates were washed in the same manner as in Example 1, then the solution of each of the detection antibodies was dispensed in each well, and then the plates were incubated at 4° C. for three hours. The plates were washed, then a chromogenic substrate solution was dispensed to each well, and then the plates were incubated, and then the absorbance at 405 nm was measured, in the same manner as in Example 1.

(3) Processing of Data

A calibration curve was produced for each of the plates. One example of the calibration curve for each of the detection antibodies is shown in each of FIGS. 5A and 5B. The value for a LAP-D in each of the 20-fold-diluted plasma specimens was obtained from each of the calibration curves. A value obtained by multiplying the value for the LAP-D by 20 was employed as a value of the concentration of the LAP-D in each of the plasma specimens. When a value obtained from the calibration curve is a negative value, the value was deemed as "0 pM". The graphs of the concentrations of LAP-D in the individual plasma specimens which were measured for five patients are shown in FIGS. 6A and 6B.

(4) Results

Figure 5A:
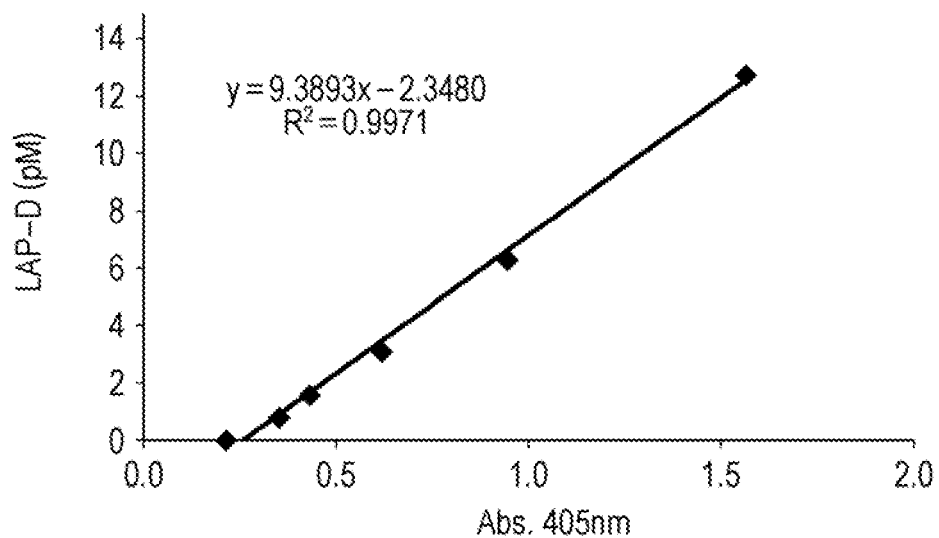
FIG. 5A shows a calibration curve produced by measuring a dilution series of a LAP-D using the isolated monoclonal antibody of the present embodiment as a detection antibody.
Figure 5B:
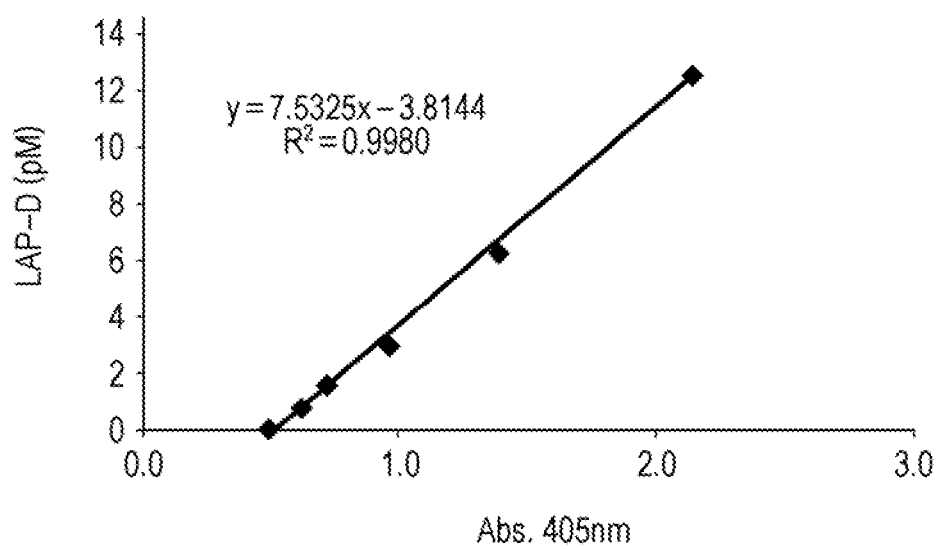
FIG. 5B shows a calibration curve produced by measuring a dilution series of a LAP-D using a commercially available anti-human LAP TGF-β1 antibody (BAM2462, manufactured by R&D Systems) as a detection antibody.
Figure 6B:
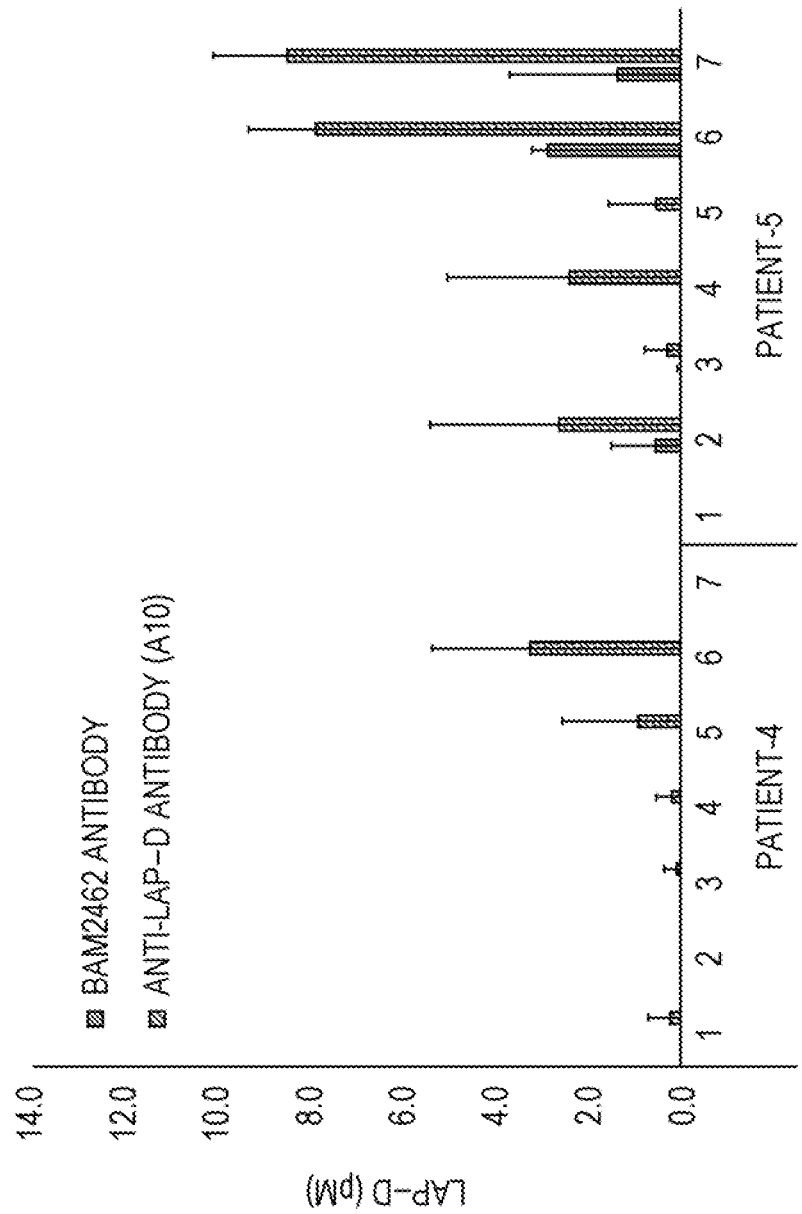
FIG. 6B is a graph showing the concentration of a LAP-D in a plasma specimen, which is produced by the measurement using the isolated monoclonal antibody of the present embodiment and an anti-human LAP TGF-β1 antibody (BAM2462, manufactured by R&D Systems) as detection antibodies.

As shown in FIGS. 5A and 5B, the slope of the calibration curve which was produced using the anti-LAP-D antibody (A10) was larger. The quantitativeness of a LAP-D in the measurement using the anti-LAP-D antibody (A10) was equivalent to or more than that in the measurement using the BAM2462 antibody. As apparent from FIGS. 6A and 6B, many specimens in which the LAP-D was detected were confirmed only when the anti-LAP-D antibody (A10) was used as a detection antibody. From these results, it was demonstrated that, when it was intended to measure a LAP-D in a biological sample such as a plasma specimen, an ELISA method using the anti-LAP-D antibody (A10) was useful.

[Example 3] Analysis of Amino Acid Sequence for Anti-LAP-D Antibody (A10)

(1) Preparation of RACE-Ready cDNA Library

A frozen stock of an anti-LAP-D antibody (A10)-producing hybridoma (1×10⁷ cells/vial, one bottle) was thawed, and the resultant solution was centrifuged at 500 g for 5 minutes to remove a supernatant from the solution, thereby obtaining cells. mRNA was prepared from the cells using GENELUTE Direct mRNA Miniprep Kit (manufactured by Sigma-Aldrich). The mRNA thus produced was measured using a nucleic acid quantification apparatus "NANODROP 2000" (manufactured by Thermo Fisher Scientific) to quantify the concentration of the mRNA. RACE-Ready cDNA was prepared from 100 μg of the mRNA using SMARTER RACE5'/3'Kit (manufactured by Clontech). As a primer, a 5'-CDR primer included in the kit was used.

(2) Amplification of Antibody Gene

An antibody gene (heavy chains and light chains) was amplified using 200 ng of the RACE-Ready cDNA as a template and using a DNA polymerase "KOD Plus neo" (manufactured by TOYOBO) on a scale of 50 μL. As a forward primer, a 1/10 volume of Universal Primier Mix included in SMARTER RACE5'/3'Kit was used. As reverse primers, three primers for light chains and three primers for heavy chains were respectively used. The composition of a reaction solution was prepared in accordance with the manual included in the kit. The reaction conditions were as follows: a denaturation procedure at 94° C. for 2 minutes was carried out, and then a two-step procedure including at 96° C. for 10 seconds and 68° C. for 80 seconds was carried out 35 cycles.

(3) Analysis of Sequence for Antibody Gene

An amplification product of the PCR was electrophoresed at 100 V for 30 minutes in a 2% agarose gel (containing 1/20000 GELGREEN Nucleic Acid Gel Stain (manufactured by Biotium)). After the electrophoresis, a band of an amplification product corresponding to each of the reverse primers was excised from the gel under the irradiation with a green LED. DNA was extracted from the gel containing the band using WIZARD SV Gel and Clean-Up System (manufactured by Promega). The analysis of the nucleotide sequence for the DNA was outsources to Eurofins Genomics K.K. Three pieces of sequence information on the light chain and three pieces of sequence information on the heavy chain were analyzed using an analysis software Genetyx Ver.14.1 (Genetyx Corporation), and the pieces of sequence information on the light chain and the pieces of sequence information on the heavy chain each were automatically integrated.

(4) Results

The amino acid sequences for the light chain and the heavy chain in the anti-LAP-D antibody (A10) are as follows.

```
Light chain
                                          (SEQ ID NO: 20)
MDMRVPAHVFGLLLLWFPGTRCDIQMTQSPSSLSASLGERVSLTCRAS

HEISGYLGWLQRQPDGTIKRLIYAASTLDSGVPKRFSGSRSGSDYSLTIS

SLESEDFADYYCLQYASYPFTFGSGTKLEVKRADAAPTVSIFPPSSEQLT

SGGASVVCFLNNFYPKDINVKWKIDGSERQNGVLNSWTDQDSKDSTYSMS

STLTLTKDEVERHNSYTCEATHKTSTSPIVKSFNRNEC

Heavy chain
                                          (SEQ ID NO: 21)
MGWSSIILFLVATATGVHSQVQLQQPGAELVRPGASVKLSCKTSGYSF

TRFWMNWVRQRPGQGLEWIGMIHSSDSITRLNQKFKDKATLTLDYSSSTA

YMQLSSPTSEDSAVYYCARGYDEYSAMDYWGQGTSVPVSSAKTTPPSVYP

LAPGSAAQTNSMVTLGCLVKGYFPEPVTVTWNSGSLSSGVHTFPAVLQSD

LYTLSSSVTVPSSTWPSETVTCNVAHPASSTKVDKKIVPRDCGCKPCICT

VPEVSSVFIFPPKPKDVLTITLTPKVTCVVVDISKDDPEVQFSWFVDDVE

VHTAQTQPREEQFNSTFRSVSELPIMHQDWLNGKEFKCRVNSAAFPAPIE

KTISKTKGRPKAPQVYTIPPPKEQMAKDKVSLTCMITDFFPEDITVEWQW

NGQPAENYKNTQPIMDTDGSYFVYSKLNVQKSNWEAGNTFTCSVLHEGLH

NHHTEKSLSHSPGK
```

The amino acid sequences for the light chain variable region and the heavy chain variable region in the anti-LAP-D antibody (A10) are as follows.

```
Light chain variable region
                                          (SEQ ID NO: 18)
DIQMTQSPSSLSASLGERVSLTCRASHEISGYLGWLQRQPDGTIKRLIYA
ASTLDSGVPKRFSGSRSGSDYSLTISSLESEDFADYYCLQYASYPFTFGS
GTKLEVKRA Heavy chain variable region
                                          (SEQ ID NO: 19)
QVQLQQPGAELVRPGASVKLSCKTSGYSFTRFWMNWVRQRPGQGLE
WIGMIHSSDSITRLNQKFKDKATLTLDYSSSTAYMQLSSPTSEDSAVYYCA
RGYDEYSAMDYWGQGTSVPVSS
```

The amino acid sequences for CDR1, CDR2 and CDR3 in the light chain and CDR1, CDR2 and CDR3 in the heavy chain in the anti-LAP-D antibody (A10) are as follows. The amino acid sequences for these CDRs are sequences based on the Kabat classification.

```
Light chain CDR1:
                                          (SEQ ID NO: 12)
RASHEISGYLG Light chain CDR2:
                                          (SEQ ID NO: 13)
AASTLDS Light chain CDR3:
                                          (SEQ ID NO: 14)
LQYASYPFT Heavy chain CDR1:
                                          (SEQ ID NO: 15)
RFWMN Heavy chain CDR2:
                                          (SEQ ID NO: 16)
MIHSSDSITRLNQKFKD Heavy chain CDR3:
                                          (SEQ ID NO: 17)
GYDEYSAMDY
```

[Example 4] Evaluation of Reactivity of Anti-LAP-D Antibody (A10)

The present inventors produced an anti-LAP-D monoclonal antibody (referred to as "A2D109 antibody", hereinafter) that is different from the anti-LAP-D antibody (A10), and have clearly demonstrated that the A2D109 antibody can bind to an integrin binding site of a LAP-D by the X-ray crystal structure analysis of the antibody (see the below-mentioned Reference Example). The A2D109 antibody has light chain CDR1 to CDR3 respectively consisting of the amino acid sequences of SEQ ID NOs: 4 to 6; and heavy chain CDR1 to CDR3 respectively consisting of the amino acid sequences of SEQ ID NOs: 7 to 9. The A2D109 antibody comprises: a light chain comprising a variable region consisting of the amino acid sequence of SEQ ID NO: 10; and a heavy chain including a variable region consisting of the amino acid sequence of SEQ ID NO: 11. In order to evaluate the reactivity of the anti-LAP-D antibody (A10), it was examined as to whether or not the anti-LAP-D antibody (A10) competed with A2D109 for the binding to a LAP-D by an SPR analysis using BIACORE (registered trademark) device. For comparison, the same analysis was also carried out using the BAM2462 antibody.

(1) Conditions for Test
(1.1) Preparation of Antigen (Analyte)
Preparation of Human TGF-β1 LAP-D A polynucleotide comprising a sequence in which a linker sequence capable of being cut with TEV protease and a His tag were added to a gene sequence encoding TGF-β1-LAP (amino acid residues position-30 to position-390) was linked to the downstream of an lgk signal, and the resultant polynucleotide was expressed in a HEK293F cell using a pOrip vector. TGF-β1-LAP was purified from a soluble fraction using HISTRAP (manufactured by GE healthcare) in accordance with the manufacturer's written usage instructions. The His tag was cut out with TEV protease, and the resultant TGF-β1-LAP was loaded onto the HISTRAP column again, and a fraction passing through the column was collected. The fraction was purified in the conventional manner through a cation exchange column (HITRAP SPHP, manufactured by GE Healthcare) to prepare a human TGF-β1 LAP-D. The molecular weight of the human TGF-β1 LAP-D was 41653 Da.

Preparation of Complex of Human TGF-β1 LAP-D and A2D109 Antibody Fab Fragment

A Fab fragment (A2D109 Fab) was prepared from the A2D109 antibody using Pierce (trademark) Mouse IgG1 Fab and F(ab')2 Preparation Kit (manufactured by Thermo Fisher). The concrete operation of the procedure was carried out in accordance with the manual included in the kit. A reaction solution produced by the procedure was purified by gel filtration using SUPERDEX 200 Increase 10/300 GL (manufactured by GE Healthcare). A 50-kDa elution fraction was collected, and the fraction was used as A2D109 Fab. Purified recombinant TGF-β1-LAP and purified A2D109 Fab were mixed together at a molar mixing ratio of 1:1. A complex thus produced was purified by gel filtration chromatography (HiLoad 16/600 SUPERDEX 200 pg, manufactured by GE Healthcare) using a column equilibrated with a buffer composed of 20 mM Tris-HCl (pH 8.0), 150 mM NaCl and 10% glycerol. The complex had a molecular weight of 89514 Da.

(1.2) Measurement using BIACORE (registered trademark)

Figure 7A:
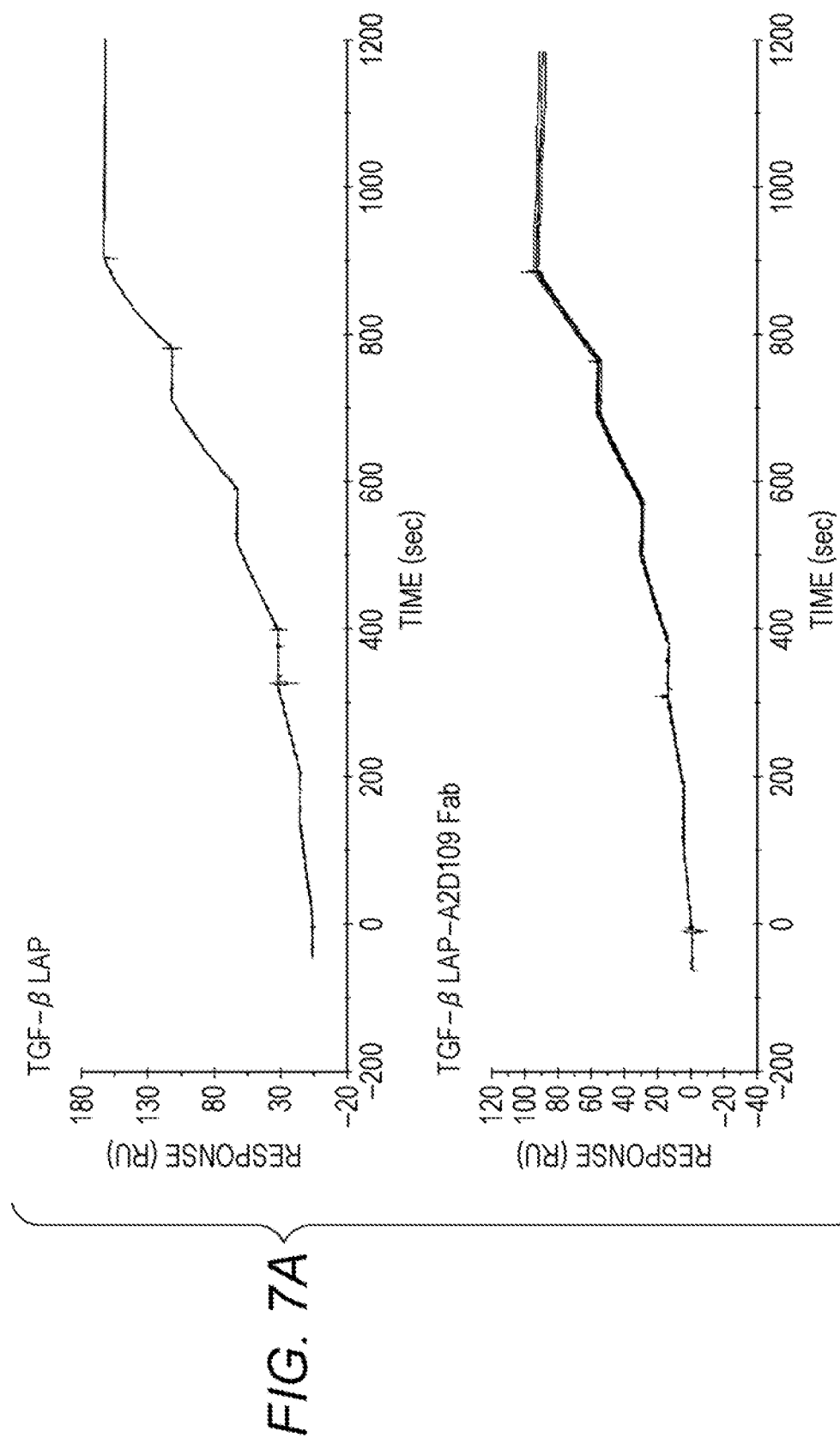
FIG. 7A is a sensorgram showing the reactivity of a commercially available anti-human LAP TGF-β1 antibody (BAM2462, manufactured by R&D Systems), which is produced by the measurement using BIACORE (registered trademark)
Figure 7B:
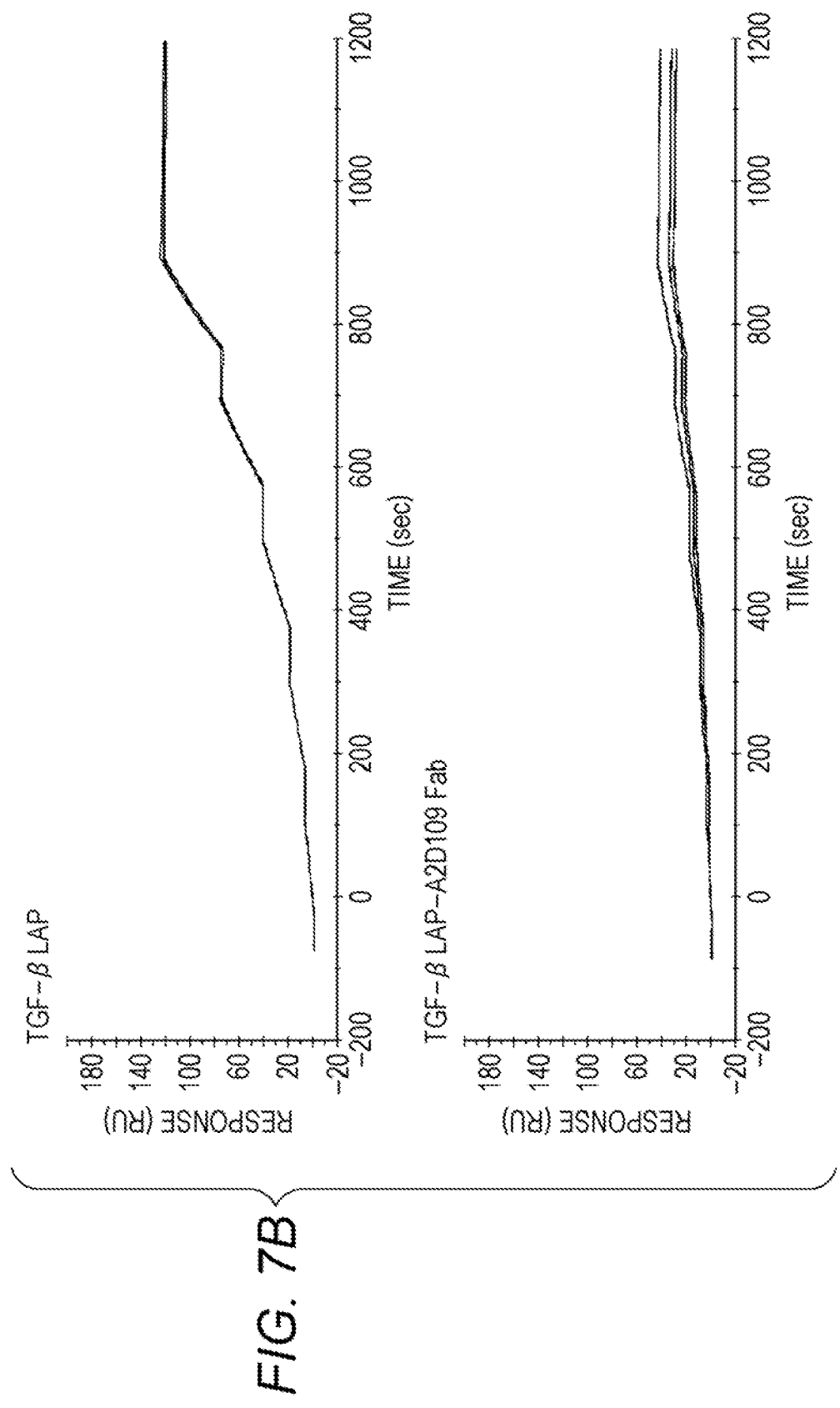
FIG. 7B is a sensorgram showing the reactivity of the isolated monoclonal antibody of the present embodiment, which is produced by the measurement using BIACORE (registered trademark).

Each of the anti-LAP-D antibody (A10) and the BAM2462 antibody was immobilized on a BIACORE (registered trademark) sensor chip Series S Sensor Chip CM5 (manufactured by GE Healthcare). The amounts of these antibodies immobilized were 2027 RU and 310 RU, respectively. Each of a solution of human TGF-β1 LAP and a solution of a complex of human TGF-β1 LAP and A2D109 Fab was diluted with a buffer composed of 10 mM of HEPES-NaOH (pH 7.5), 150 mM of NaCl, 3 mM of EDTA and 0.005% of Surfactant P-20 to prepare solutions having various concentrations. Each of these solutions was fed to BIACORE (registered trademark) T200 (manufactured by GE Healthcare). The analyte concentration in each of the solutions and the measurement conditions are shown below. Measurement data were analyzed using BIACORE (registered trademark) Evaluation software to acquire date on the affinity of each of the antibodies. Sensorgrams are shown in FIGS. 7A and 7B. Parameters are shown in Table 1.

[Analyte Concentrations]
1.56 nM, 3.13 nM, 6.25 nM, 12.5 nM and 25 nM

[Measurement Conditions]
Association: 30 μL/min, 60 sec
Dissociation: 30 μL/min, 60 sec
Regeneration: Gly-HCl (pH 1.5)/60 μL/min, 60 sec

TABLE 1

| Ligand | Analyte | ka (1/Ms) | kd (1/s) | KD (M) | Rmax (RU) | Chi$^2$ (RU$^2$) | U-value |
|---|---|---|---|---|---|---|---|
| BAM2462 | TGF-β LAP | 1.40E+06 | 2.34E−05 | 1.67E−11 | 174.2 | 0.373 | 20 |
|  | TGF-β LAP-A2D109Fab | 4.47E+05 | 1.54E−04 | 3.45E−10 | 150.5 | 0.916 | 7 |
| A10 | TGF-β LAP | 1.95E+05 | 4.17E−05 | 2.14E−10 | 178.4 | 0.631 | 15 |
|  | TGF-β LAP-A2D109Fab | 3.04E+05 | 2.01E−04 | 5.64E−10 | 43.53 | 0.171 | 3 |

An Rmax residual ratio (%) was calculated from an Rmax value of binding of each of the anti-LAP-D antibody (A10) and the BAM2462 antibody to each of the antigens (analytes) in accordance with the formula shown below. An Rmax residual ratio (%) with taking the antigen:antibody molecular weight ratio into consideration was also calculated. The results are shown in Table 2.

(Rmax residual ratio)=[(Rmax value of binding between antibody and complex of LAP-D and A2D109 Fab)/(Rmax value of binding between antibody and LAP-D)]×100

(Rmax residual ratio with taking molecular weight ratio into consideration)=[(Rmax value of binding between antibody and complex of LAP-D and A2D109 Fab)/(molecular weight of complex of LAP-D and A2D109 Fab)]/[(Rmax value of binding between antibody and LAP-D)/(molecular weight of LAP-D)]×100

TABLE 2

| Ligand | Analyte | Rmax (RU) | Rmax residual ratio | Rmax residual ratio (Rmax residual ratio with taking molecular weight ratio into consideration) |
|---|---|---|---|---|
| BAM2462 | TGF-β LAP | 174.2 | — | — |
|  | TGF-β LAP-A2D109Fab | 150.5 | 86.4% | 40.2% |
| A10 | TGF-β LAP | 178.4 | — | — |
|  | TGF-β LAP-A2D109Fab | 43.53 | 24.4% | 11.4% |

As shown in Table 2, the reactivity of the BAM2462 antibody in the presence of the A2D109 antibody (reference antibody) was remained by 86.4% relative to that in the absence of the reference antibody, while the reactivity of the anti-LAP-D antibody (A10) was decreased to 24.4% due to the presence of the A2D109 antibody. Namely, the Rmax value of binding between the anti-LAP-D antibody (A10) and the LAP-D in the presence of the reference antibody was decreased by 75.6% compared with that in the absence of the reference antibody. As shown in FIG. 7A, in the sensorgram for the binding of the BAM2462 antibody to the LAP-D, the response was increased both in the presence of the A2D109 antibody and the absence of the A2D109 antibody. In contrast, as shown in FIG. 7B, in the sensorgram for the binding of the anti-LAP-D antibody (A10) to the LAP-D, the response was not increased so greatly due to the presence of the A2D109 antibody. From these results, it was suggested that the epitope of the anti-LAP-D antibody (A10) was the same as the epitope of the A2D109 antibody or was located in the vicinity of the epitope of the A2D109 antibody.

[Reference Example] X-Ray Crystal Structure Analysis of Complex of A2D109 Antibody Fv Fragment and TGF-β1-LAP (C33S/N176Q)

(1) Conditions for Test
(1.1) Expression and Purification of TGF-β1-LAP (C33S/N176Q)

A TGF-β1-LAP (amino acid residues at position-30 to position-390) which was fused to a His tag through a linker capable of being cut with TEV protease and to which a mutation (C33S/N176Q) was introduced into two sites was linked to the downstream of an lgk signal, and the resultant product was expressed in a HEK293F cell using a pOrip vector. The TGF-β1-LAP was purified from a soluble fraction using HISTRAP (manufactured by GE healthcare) in accordance with the manufacturer's written usage instructions. The His tag was cut with TEV protease, then the resultant TGF-β1-LAP was loaded onto the HISTRAP column again, then a fraction passing through the column was collected, and then the TGF-β1-LAP was prepared in the conventional manner using a cation exchange column (HI-TRAP SP HP, manufactured by GE Healthcare).

(1.2) Expression and Purification of A2D109 Antibody Fv Fragment (A2D109 Fv)

An A2D109 Fv (heavy chain and light chain) which was fused to a His tag through a linker capable of being cut with TEV protease was expressed in an E. coli cell-free system using a pCR.2.1 vector. A soluble fraction was passed through a HISTRAP column (manufactured by GE healthcare) to purify A2D109 Fv. The His tag was cut out with TEV protease, then the resultant A2D109 Fv was loaded onto the HISTRAP column again, then a fraction passing through the column was collected, and the A2D109 Fv was further purified using an anion exchange column (HITRAP Q HP, manufactured by GE Healthcare). A fraction containing the Fv was pooled and was stored at −80° C.

(1.3) Preparation of Complex of A2D109 Fv and TGF-β1-LAP (C33S/N176Q)

The purified recombinant TGF-β1-LAP and the purified Fv were mixed together at a molar mixing ratio of 1:1.2. A complex thus produced was purified by gel filtration chromatography (HiLoad 16/600 SUPERDEX 200 pg, manufactured by GE Healthcare) using a column equilibrated with a buffer composed of 20 mM of Tris-HCl (pH 8.0), 150 mM of NaCl and 10% of glycerol.

(1.4) Crystallization

The purified complex was concentrated to about 6 mg/mL, and was then crystallized by a sitting drop vapor diffusion crystallization method combined with a seeding method at 25° C. A reservoir solution used was composed of 25% w/v of polyethylene glycol 3350 and 0.1 M of HEPES (pH 7.5). In this manner, a plate-like crystal was obtained successfully in about 1 week. The crystal was immersed in a solution composed of 25% w/v of polyethylene glycol 3350, 0.1 M of HEPES (pH 7.5) and 5% of glycerol.

(1.5) Collection of Data and Determination of Structure

X-ray diffraction data was measured by employing BL32XU in SPring-8. During the measurement, the crystal was placed under the nitrogen stream at −178° C. at all time to keep the frozen state of the crystal, and X-ray diffraction images (1800 images in total) were collected using a PAD (EIGER-9M) detector connected to a beam line while rotating the crystal at an angle of 0.1° per one rotation. The determination of a cell parameter, the indexing of a diffraction spot and the processing of diffraction data acquired from the diffraction images were carried out using a XDS package (Acta. Cryst. D66:125-132 (2010)). In this manner, diffraction intensity data at a resolution of 2.93 Å were acquired eventually. The crystallographic data statistic values are shown in Table 3.

The structure was determined by molecular replacement using a program Phaser (J. Appl. Cryst. 40:658-674 (2007)). The search model for TGF-β1 was derived from a disclosed pro-TGF-β1 crystal structure (PDB code: 3RJR), and the search model for the Fv was derived from an Fv region of a disclosed norovirus crystal structure (PDB code: 4NCC). Each of these models was constructed using Coot program (Acta. Cryst. D66:486-501 (2010)) and was then refined using a program Phenix (Acta. Cryst. D66:213-221 (2010)). The crystallographic reliability factor (R) of the diffraction intensity data at 46.71-2.93 Å was 22.14%, and the Free R value was 29.76%. The structure refinement statistic values are shown in Table 3.

TABLE 3

Collection of X-ray data and refinement statistic values

Collection of data

| | |
|---|---|
| Space group | P2₁ |
| Unit cell | |
| a, b, c (Å) | 86.85, 160.58, 95.76 |
| α, β, γ (°) | 90, 92.97, 90 |
| Resolution (Å) | 46.71-2.93 |
| Number of total reflections | 195841 |
| Number of independent reflections | 55631 |
| Completeness (outermost shell) (%) | 98.73 (97.38) |
| $R_{merge}{}^a$ (outermost shell) (%) | 10.5 (96.2) |

Refinement

| | |
|---|---|
| Resolution (Å) | 46.71-2.93 |
| Number of reflections | 54068 |
| R factor$^b$ ($R_{free}{}^c$) (%) | 22.14 (29.76) |
| rms deviation from desired value | |
| Bond distance (Å) | 0.011 |
| Bond angle (°) | 1.394 |

$^a$; $R_{merge} = \Sigma\,hkl\,\Sigma j\,|\,IJ\,(hkl)\text{-}<I\,(hkl)>|\,/\,\Sigma\,hkl\,\Sigma\,j\,|\,Ij\,(hkl)|$, wherein Ij (hki) and <I (hkl)> respectively represent the intensity of a measurement j having an index hkl and the average intensities of reflections of the measurement j.
$^b$; R factor = $\Sigma\,hkl\,|\,F_{calc}\,(hkl)\,|\text{-}|\,F_{obs}\,(hkl)\,|\,/\,\Sigma\,hkl\,|\,F_{obs}\,(hkl)\,|$, wherein $F_{obs}$ and $F_{calc}$ respectively represent a found amplitude and a calculated amplitude of the structure factor.
$^c$; $R_{free}$ is calculated using a value corresponding to 3.6% of the reflection that is randomly excluded.

(2) Results

As the results of the above-mentioned structure determination, it was found that the A2D109 antibody binding site was an RGD sequence that was an integrin binding site of a human TGF-β1 LAP-D.

SEQUENCE LISTING

Japanese Patent Application No. 19-009JP2019-133839_3.app

---

What is claimed is:

1. A monoclonal antibody that binds a human Transforming Growth Factor-β (TGF-β) Latency Associated Protein (LAP) degradate, the monoclonal antibody being capable of recognizing an integrin binding site in the human TGF-β LAP degradate,
   wherein the monoclonal antibody comprises: a light chain comprising CDR1, CDR2 and CDR3 consisting of the amino acid sequences of SEQ ID NOs: 12, 13 and 14, respectively; and a heavy chain comprising CDR1, CDR2 and CDR3 consisting of the amino acid sequences of SEQ ID NOs: 15, 16 and 17, respectively.

2. The monoclonal antibody according to claim 1, wherein the integrin binding site comprises an RGD sequence.

3. The monoclonal antibody according to claim 1, wherein the monoclonal antibody recognizes a region comprising amino acid residues at position-215 to position-217 in the amino acid sequence of SEQ ID NO: 2.

4. The monoclonal antibody according to claim 1, wherein the monoclonal antibody competes with a reference antibody which comprises: a light chain comprising CDR1, CDR2 and CDR3 consisting of the amino acid sequences of SEQ ID NOs: 4, 5 and 6, respectively; and a heavy chain comprising CDR1, CDR2 and CDR3 consisting of the amino acid sequences of SEQ ID NOs: 7, 8 and 9, respectively.

5. The monoclonal antibody according to claim 4, wherein an Rmax value of binding between the monoclonal antibody and the LAP degradate is decreased by at least 70% in the presence of the reference antibody, the Rmax value being measured using a surface plasmon resonance analysis device.

6. The monoclonal antibody according to claim 1, wherein the monoclonal antibody comprises: a light chain comprising a variable region consisting of the amino acid sequence of SEQ ID NO: 18; and a heavy chain comprising a variable region consisting of the amino acid sequence of SEQ ID NO: 19.

7. The monoclonal antibody according to claim 1, wherein the monoclonal antibody comprises: a light chain comprising the amino acid sequence of SEQ ID NO: 20; and a heavy chain comprising the amino acid sequence of SEQ ID NO: 21.

8. A reagent for use in detection of a LAP degradate, the reagent comprising the monoclonal antibody according to claim 1.

9. A composition comprising the monoclonal antibody of claim 1.

10. A method for measuring a human TGF-β LAP degradate, comprising measuring a TGF-β LAP degradate in a biological sample collected from a subject using the monoclonal antibody according to claim 1.

11. The method according to claim 10, wherein the integrin binding site comprises an RGD sequence.

12. A method for monitoring a measurement value for a human TGF-β LAP degradate, comprising:
    measuring a TGF-β LAP degradate in a first biological sample collected from a subject using the monoclonal antibody according to claim 1; and
    measuring the TGF-β LAP degradate in a second biological sample collected from the subject using the monoclonal antibody,
    wherein the first biological sample is a biological sample collected from the subject at a first point of time and the second biological sample is a biological sample collected from the subject at a second point of time that is different from the first point of time.

* * * * *

SEQUENCE LISTING

<160> NUMBER OF SEQ ID NOS: 22

<210> SEQ ID NO 1
<211> LENGTH: 390
<212> TYPE: PRT
<213> ORGANISM: Homo sapiens

<400> SEQUENCE: 1

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
            245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
            275                 280                 285

Thr Glu Lys Asn Cys Cys Val Arg Gln Leu Tyr Ile Asp Phe Arg Lys
290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
            325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
370                 375                 380

Arg Ser Cys Lys Cys Ser
385                 390

<210> SEQ ID NO 2
<211> LENGTH: 249
<212> TYPE: PRT
<213> ORGANISM: Homo sapiens

<400> SEQUENCE: 2

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn

```
              195                 200                 205
Gly Phe Thr Thr Gly Arg Arg Gly Asp Leu Ala Thr Ile His Gly Met
        210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg
                245
```

<210> SEQ ID NO 3
<211> LENGTH: 220
<212> TYPE: PRT
<213> ORGANISM: Homo sapiens

<400> SEQUENCE: 3

```
Leu Ala Ser Pro Pro Ser Gln Gly Glu Val Pro Pro Gly Pro Leu Pro
1               5                   10                  15

Glu Ala Val Leu Ala Leu Tyr Asn Ser Thr Arg Asp Arg Val Ala Gly
            20                  25                  30

Glu Ser Ala Glu Pro Glu Pro Glu Pro Glu Ala Asp Tyr Tyr Ala Lys
        35                  40                  45

Glu Val Thr Arg Val Leu Met Val Glu Thr His Asn Glu Ile Tyr Asp
50                  55                  60

Lys Phe Lys Gln Ser Thr His Ser Ile Tyr Met Phe Phe Asn Thr Ser
65                  70                  75                  80

Glu Leu Arg Glu Ala Val Pro Glu Pro Val Leu Leu Ser Arg Ala Glu
            85                  90                  95

Leu Arg Leu Leu Arg Leu Lys Leu Lys Val Glu Gln His Val Glu Leu
            100                 105                 110

Tyr Gln Lys Tyr Ser Asn Asn Ser Trp Arg Tyr Leu Ser Asn Arg Leu
        115                 120                 125

Leu Ala Pro Ser Asp Ser Pro Glu Trp Leu Ser Phe Asp Val Thr Gly
    130                 135                 140

Val Val Arg Gln Trp Leu Ser Arg Gly Gly Glu Ile Glu Gly Phe Arg
145                 150                 155                 160

Leu Ser Ala His Cys Ser Cys Asp Ser Arg Asp Asn Thr Leu Gln Val
                165                 170                 175

Asp Ile Asn Gly Phe Thr Thr Gly Arg Arg Gly Asp Leu Ala Thr Ile
            180                 185                 190

His Gly Met Asn Arg Pro Phe Leu Leu Leu Met Ala Thr Pro Leu Glu
        195                 200                 205

Arg Ala Gln His Leu Gln Ser Ser Arg His Arg Arg
    210                 215                 220
```

<210> SEQ ID NO 4
<211> LENGTH: 10
<212> TYPE: PRT
<213> ORGANISM: Mus musculus

<400> SEQUENCE: 4

```
Ser Ala Ser Ser Ser Val Ser Tyr Met His
1               5                   10
```

<210> SEQ ID NO 5
<211> LENGTH: 7
<212> TYPE: PRT
<213> ORGANISM: Mus musculus

<400> SEQUENCE: 5

Ser Thr Ser Asn Leu Ala Ser
1               5

<210> SEQ ID NO 6
<211> LENGTH: 9
<212> TYPE: PRT
<213> ORGANISM: Mus musculus

<400> SEQUENCE: 6

Gln Gln Arg Ser Ser Tyr Pro Phe Thr
1               5

<210> SEQ ID NO 7
<211> LENGTH: 5
<212> TYPE: PRT
<213> ORGANISM: Mus musculus

<400> SEQUENCE: 7

Ser Tyr Trp Met Asn
1               5

<210> SEQ ID NO 8
<211> LENGTH: 17
<212> TYPE: PRT
<213> ORGANISM: Mus musculus

<400> SEQUENCE: 8

Met Ile Asp Pro Ser Asp Ser Glu Thr His Tyr Asn Gln Met Phe Lys
1               5                   10                  15
Asp

<210> SEQ ID NO 9
<211> LENGTH: 7
<212> TYPE: PRT
<213> ORGANISM: Mus musculus

<400> SEQUENCE: 9

Trp Pro Tyr Ala Leu Asp Tyr
1               5

<210> SEQ ID NO 10
<211> LENGTH: 108
<212> TYPE: PRT
<213> ORGANISM: Mus musculus

<400> SEQUENCE: 10

Gln Ile Val Leu Thr Gln Ser Pro Ala Ile Met Ser Ala Ser Pro Gly
1               5                   10                  15
Glu Lys Val Thr Met Thr Cys Ser Ala Ser Ser Ser Val Ser Tyr Met
                20                  25                  30
His Trp Phe Gln Gln Lys Pro Gly Thr Ser Pro Lys Leu Trp Ile Tyr
            35                  40                  45
Ser Thr Ser Asn Leu Ala Ser Gly Val Pro Ala Arg Phe Ser Gly Ser
        50                  55                  60
Gly Ser Gly Thr Ser Tyr Ser Leu Thr Ile Ser Arg Met Glu Ala Glu
65                  70                  75                  80
Asp Ala Ala Thr Tyr Tyr Cys Gln Gln Arg Ser Ser Tyr Pro Phe Thr
                85                  90                  95
Phe Gly Ser Gly Thr Lys Leu Glu Ile Lys Arg Ala
            100                 105

<210> SEQ ID NO 11
<211> LENGTH: 116
<212> TYPE: PRT
<213> ORGANISM: Mus musculus

<400> SEQUENCE: 11

Glu Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Gly Gln Gly Leu Glu Trp Ile
        35                  40                  45

Gly Met Ile Asp Pro Ser Asp Ser Glu Thr His Tyr Asn Gln Met Phe
    50                  55                  60

Lys Asp Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Val Asn Trp Pro Tyr Ala Leu Asp Tyr Trp Gly Gln Gly Thr Ser Val
            100                 105                 110

Thr Val Ser Ser
        115

<210> SEQ ID NO 12
<211> LENGTH: 11
<212> TYPE: PRT
<213> ORGANISM: Mus musculus

<400> SEQUENCE: 12

Arg Ala Ser His Glu Ile Ser Gly Tyr Leu Gly
1               5                   10

<210> SEQ ID NO 13
<211> LENGTH: 7
<212> TYPE: PRT
<213> ORGANISM: Mus musculus

<400> SEQUENCE: 13

Ala Ala Ser Thr Leu Asp Ser
1               5

<210> SEQ ID NO 14
<211> LENGTH: 9
<212> TYPE: PRT
<213> ORGANISM: Mus musculus

<400> SEQUENCE: 14

Leu Gln Tyr Ala Ser Tyr Pro Phe Thr
1               5

<210> SEQ ID NO 15
<211> LENGTH: 5
<212> TYPE: PRT
<213> ORGANISM: Mus musculus

<400> SEQUENCE: 15

Arg Phe Trp Met Asn
1               5

<210> SEQ ID NO 16
<211> LENGTH: 17

```
<212> TYPE: PRT
<213> ORGANISM: Mus musculus

<400> SEQUENCE: 16

Met Ile His Ser Ser Asp Ser Ile Thr Arg Leu Asn Gln Lys Phe Lys
1               5                   10                  15

Asp

<210> SEQ ID NO 17
<211> LENGTH: 10
<212> TYPE: PRT
<213> ORGANISM: Mus musculus

<400> SEQUENCE: 17

Gly Tyr Asp Glu Tyr Ser Ala Met Asp Tyr
1               5                   10

<210> SEQ ID NO 18
<211> LENGTH: 109
<212> TYPE: PRT
<213> ORGANISM: Mus musculus

<400> SEQUENCE: 18

Asp Ile Gln Met Thr Gln Ser Pro Ser Ser Leu Ser Ala Ser Leu Gly
1               5                   10                  15

Glu Arg Val Ser Leu Thr Cys Arg Ala Ser His Glu Ile Ser Gly Tyr
                20                  25                  30

Leu Gly Trp Leu Gln Arg Gln Pro Asp Gly Thr Ile Lys Arg Leu Ile
            35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Phe
                85                  90                  95

Thr Phe Gly Ser Gly Thr Lys Leu Glu Val Lys Arg Ala
            100                 105

<210> SEQ ID NO 19
<211> LENGTH: 119
<212> TYPE: PRT
<213> ORGANISM: Mus musculus

<400> SEQUENCE: 19

Gln Val Gln Leu Gln Gln Pro Gly Ala Glu Leu Val Arg Pro Gly Ala
1               5                   10                  15

Ser Val Lys Leu Ser Cys Lys Thr Ser Gly Tyr Ser Phe Thr Arg Phe
                20                  25                  30

Trp Met Asn Trp Val Arg Gln Arg Pro Gly Gln Gly Leu Glu Trp Ile
            35                  40                  45

Gly Met Ile His Ser Ser Asp Ser Ile Thr Arg Leu Asn Gln Lys Phe
    50                  55                  60

Lys Asp Lys Ala Thr Leu Thr Leu Asp Tyr Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Gly Tyr Asp Glu Tyr Ser Ala Met Asp Tyr Trp Gly Gln Gly
            100                 105                 110
```

Thr Ser Val Pro Val Ser Ser
            115

<210> SEQ ID NO 20
<211> LENGTH: 236
<212> TYPE: PRT
<213> ORGANISM: Mus musculus

<400> SEQUENCE: 20

Met Asp Met Arg Val Pro Ala His Val Phe Gly Leu Leu Leu Leu Trp
1               5                   10                  15

Phe Pro Gly Thr Arg Cys Asp Ile Gln Met Thr Gln Ser Pro Ser Ser
            20                  25                  30

Leu Ser Ala Ser Leu Gly Glu Arg Val Ser Leu Thr Cys Arg Ala Ser
        35                  40                  45

His Glu Ile Ser Gly Tyr Leu Gly Trp Leu Gln Arg Gln Pro Asp Gly
    50                  55                  60

Thr Ile Lys Arg Leu Ile Tyr Ala Ala Ser Thr Leu Asp Ser Gly Val
65                  70                  75                  80

Pro Lys Arg Phe Ser Gly Ser Arg Ser Gly Ser Asp Tyr Ser Leu Thr
                85                  90                  95

Ile Ser Ser Leu Glu Ser Glu Asp Phe Ala Asp Tyr Tyr Cys Leu Gln
            100                 105                 110

Tyr Ala Ser Tyr Pro Phe Thr Phe Gly Ser Gly Thr Lys Leu Glu Val
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Cys
225                 230                 235

<210> SEQ ID NO 21
<211> LENGTH: 462
<212> TYPE: PRT
<213> ORGANISM: Mus musculus

<400> SEQUENCE: 21

Met Gly Trp Ser Ser Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Thr Ser Gly Tyr Ser Phe
        35                  40                  45

Thr Arg Phe Trp Met Asn Trp Val Arg Gln Arg Pro Gly Gln Gly Leu
    50                  55                  60

Glu Trp Ile Gly Met Ile His Ser Ser Asp Ser Ile Thr Arg Leu Asn
65                  70                  75                  80

-continued

```
Gln Lys Phe Lys Asp Lys Ala Thr Leu Thr Leu Asp Tyr Ser Ser Ser
                85                  90                  95
Thr Ala Tyr Met Gln Leu Ser Ser Pro Thr Ser Glu Asp Ser Ala Val
            100                 105                 110
Tyr Tyr Cys Ala Arg Gly Tyr Asp Glu Tyr Ser Ala Met Asp Tyr Trp
            115                 120                 125
Gly Gln Gly Thr Ser Val Pro Val Ser Ser Ala Lys Thr Thr Pro Pro
130                 135                 140
Ser Val Tyr Pro Leu Ala Pro Gly Ser Ala Ala Gln Thr Asn Ser Met
145                 150                 155                 160
Val Thr Leu Gly Cys Leu Val Lys Gly Tyr Phe Pro Glu Pro Val Thr
                165                 170                 175
Val Thr Trp Asn Ser Gly Ser Leu Ser Ser Gly Val His Thr Phe Pro
            180                 185                 190
Ala Val Leu Gln Ser Asp Leu Tyr Thr Leu Ser Ser Ser Val Thr Val
            195                 200                 205
Pro Ser Ser Thr Trp Pro Ser Glu Thr Val Thr Cys Asn Val Ala His
210                 215                 220
Pro Ala Ser Ser Thr Lys Val Asp Lys Lys Ile Val Pro Arg Asp Cys
225                 230                 235                 240
Gly Cys Lys Pro Cys Ile Cys Thr Val Pro Glu Val Ser Ser Val Phe
                245                 250                 255
Ile Phe Pro Pro Lys Pro Lys Asp Val Leu Thr Ile Thr Leu Thr Pro
            260                 265                 270
Lys Val Thr Cys Val Val Asp Ile Ser Lys Asp Asp Pro Glu Val
                275                 280                 285
Gln Phe Ser Trp Phe Val Asp Asp Val Glu Val His Thr Ala Gln Thr
            290                 295                 300
Gln Pro Arg Glu Glu Gln Phe Asn Ser Thr Phe Arg Ser Val Ser Glu
305                 310                 315                 320
Leu Pro Ile Met His Gln Asp Trp Leu Asn Gly Lys Glu Phe Lys Cys
                325                 330                 335
Arg Val Asn Ser Ala Ala Phe Pro Ala Pro Ile Glu Lys Thr Ile Ser
            340                 345                 350
Lys Thr Lys Gly Arg Pro Lys Ala Pro Gln Val Tyr Thr Ile Pro Pro
            355                 360                 365
Pro Lys Glu Gln Met Ala Lys Asp Lys Val Ser Leu Thr Cys Met Ile
370                 375                 380
Thr Asp Phe Phe Pro Glu Asp Ile Thr Val Glu Trp Gln Trp Asn Gly
385                 390                 395                 400
Gln Pro Ala Glu Asn Tyr Lys Asn Thr Gln Pro Ile Met Asp Thr Asp
                405                 410                 415
Gly Ser Tyr Phe Val Tyr Ser Lys Leu Asn Val Gln Lys Ser Asn Trp
            420                 425                 430
Glu Ala Gly Asn Thr Phe Thr Cys Ser Val Leu His Glu Gly Leu His
            435                 440                 445
Asn His His Thr Glu Lys Ser Leu Ser His Ser Pro Gly Lys
450                 455                 460
```

```
<210> SEQ ID NO 22
<211> LENGTH: 10
<212> TYPE: PRT
<213> ORGANISM: Homo sapiens

<400> SEQUENCE: 22

Leu Ala Ser Pro Pro Ser Gln Gly Glu Val
1               5                   10
```